(12) United States Patent
Yoo

(10) Patent No.: US 8,263,386 B2
(45) Date of Patent: Sep. 11, 2012

(54) DIGITAL BIO DISC (DBD), DBD DRIVER APPARATUS, AND ASSAY METHOD USING THE SAME

(75) Inventor: Jae Chern Yoo, Pohang-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 728 days.

(21) Appl. No.: 11/919,931

(22) PCT Filed: May 6, 2006

(86) PCT No.: PCT/KR2006/001709
§ 371 (c)(1),
(2), (4) Date: Jan. 29, 2009

(87) PCT Pub. No.: WO2006/121266
PCT Pub. Date: Nov. 16, 2006

(65) Prior Publication Data
US 2009/0221431 A1    Sep. 3, 2009

(30) Foreign Application Priority Data
May 6, 2005    (KR) .................. 10-2005-0038765

(51) Int. Cl.
*C12M 1/00* (2006.01)
*C12Q 1/66* (2006.01)
*C12P 19/34* (2006.01)

(52) U.S. Cl. .................. 435/283.1; 435/6.1; 435/306.1; 435/307.1; 435/308.1; 422/50; 422/49

(58) Field of Classification Search .................. None
See application file for complete search history.

(56) References Cited

U.S. PATENT DOCUMENTS

| | | |
|---|---|---|
| 6,030,581 A | 2/2000 | Virtanen |
| 2003/0054376 A1* | 3/2003 | Mullis et al. .................. 435/6 |
| 2004/0155213 A1* | 8/2004 | Yoo .................. 251/65 |
| 2005/0069913 A1* | 3/2005 | Mian et al. .................. 435/6 |
| 2006/0040273 A1* | 2/2006 | Chaiken et al. .................. 435/6 |

FOREIGN PATENT DOCUMENTS

| | | |
|---|---|---|
| EP | 1 885 883 | 11/2006 |
| JP | 8-121636 | 5/1996 |
| JP | 2003-84001 | 3/2003 |

(Continued)

OTHER PUBLICATIONS

International Search Report (PCT/ISA/210) mailed on Sep. 5, 2006 in connection with the International Application No. PCT/KR2006/001709.

(Continued)

*Primary Examiner* — Sally Merkling
(74) *Attorney, Agent, or Firm* — Staas & Halsey LLP

(57) ABSTRACT

An aspect of embodiment relates to a digital bio disc (DBD) including new valve control means and fluid movement system, a digital bio disc (DBD) driver apparatus, and an assay method using the same. More particularly, an aspect of embodiment relates to a DBD with a lab-on-a-chip for various diagnostic assays, nucleic acid hybridization assays, or immunoassays, a DBD driver apparatus integrated with a controller for controlling the DBD and a general optical disc (CD or DVD), and an assay method using the same.

88 Claims, 12 Drawing Sheets

FOREIGN PATENT DOCUMENTS

| | | |
|---|---|---|
| JP | 2004-73995 | 3/2004 |
| WO | 02/097422 | 12/2002 |
| WO | 2003/021223 | 3/2003 |
| WO | 03/080868 A1 | 10/2003 |
| WO | 2003/080868 | 10/2003 |
| WO | WO 03/080868 | 10/2003 |
| WO | WO-03080868 * | 10/2003 |
| WO | 2006/118420 | 11/2006 |

OTHER PUBLICATIONS

Japanese Office Action issued Jan. 28, 2011 in corresponding Japanese Patent Application 2008-509943.

European Search Report issued on Jul. 21, 2009 is corresponding European Patent Application No. 06757656.1.

Japanese Office Action received Jul. 6, 2010 in corresponding Japanese Patent Application No. 2008-509943.

Ralf Lenigk et al., "Surface Characterization of a Silicon-Chip-Based DNA Microarray", Langmuir 2001, 17, American Chemical Society, pp. 2497-2501.

Hidenori Nagai et al., "High-throughput PCR in silicon based microchamber array", Biosensors & Bioelectronics 16, Elsevier Science B.V., 2001, pp. 1015-1019.

* cited by examiner

[Fig. 1]
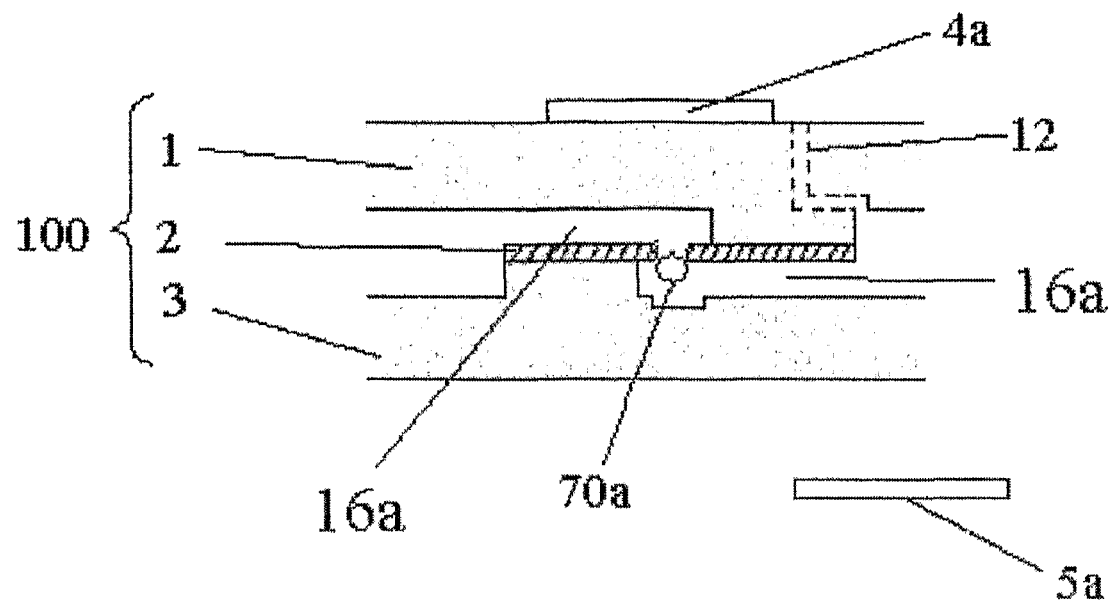
[Fig. 2]
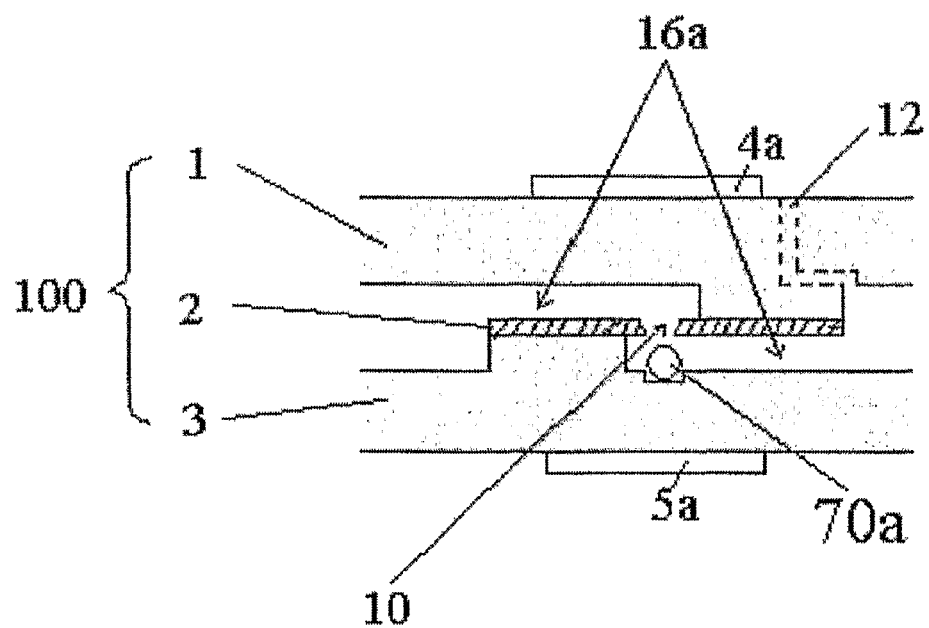

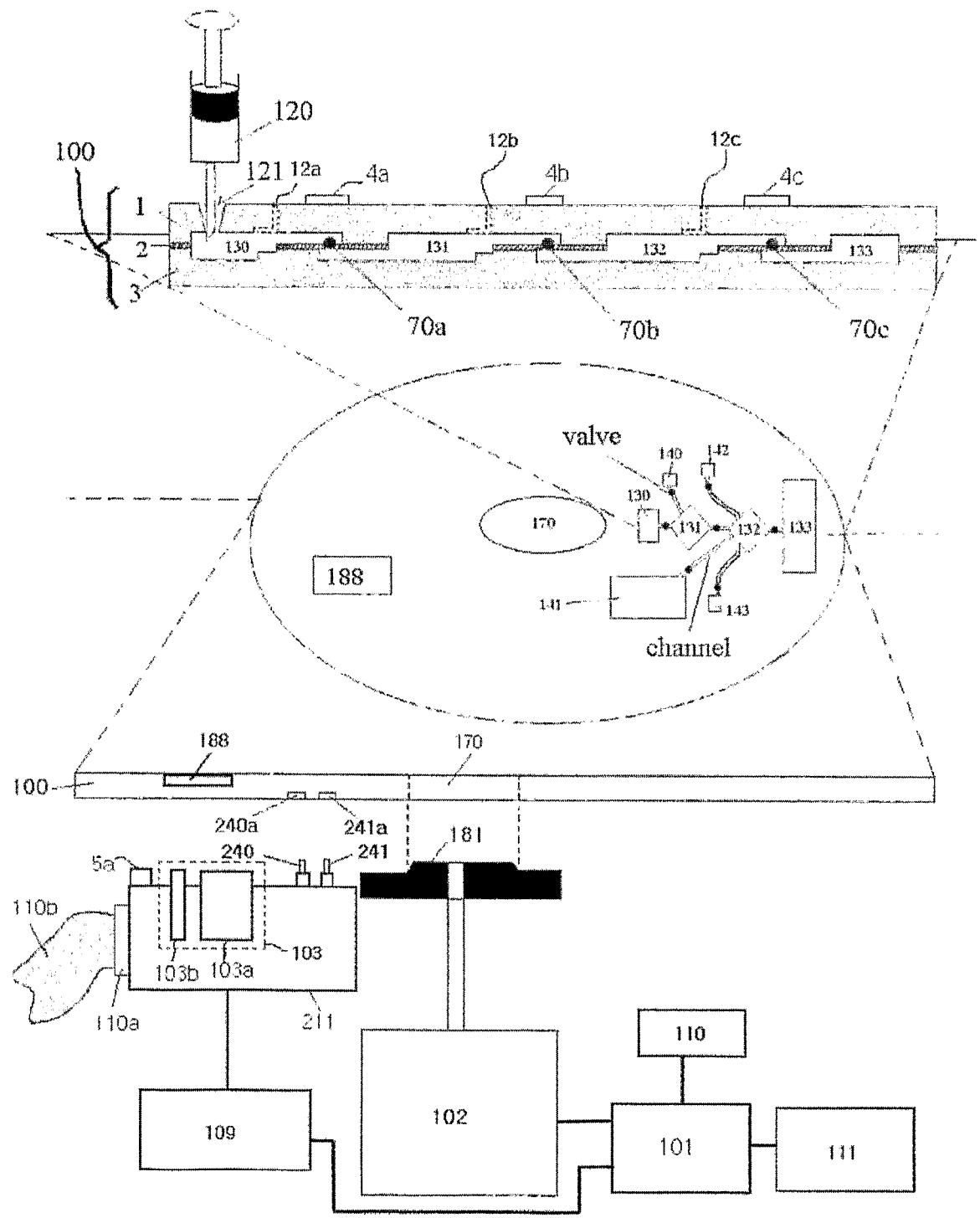
[Fig. 3]

[Fig. 4]
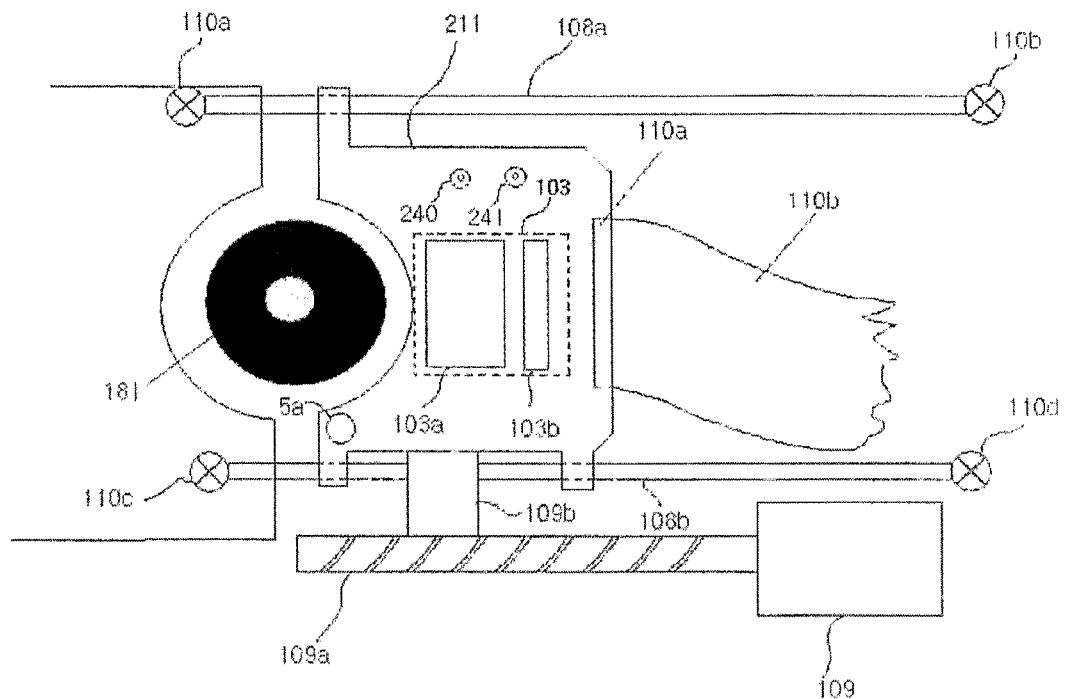
[Fig. 5]
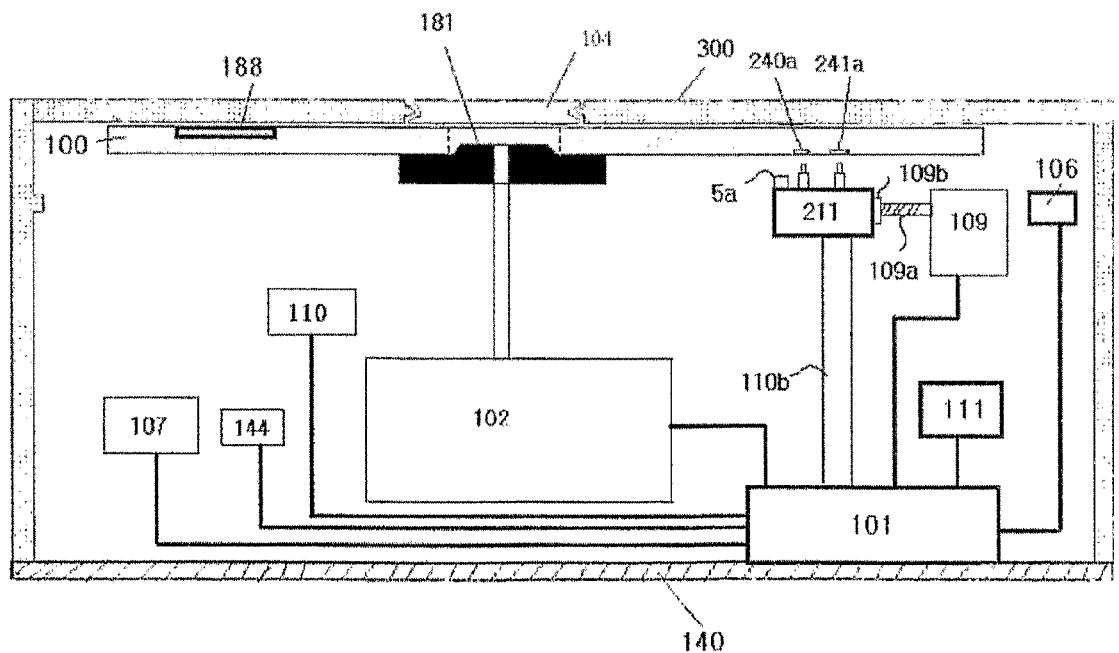

[Fig. 6]
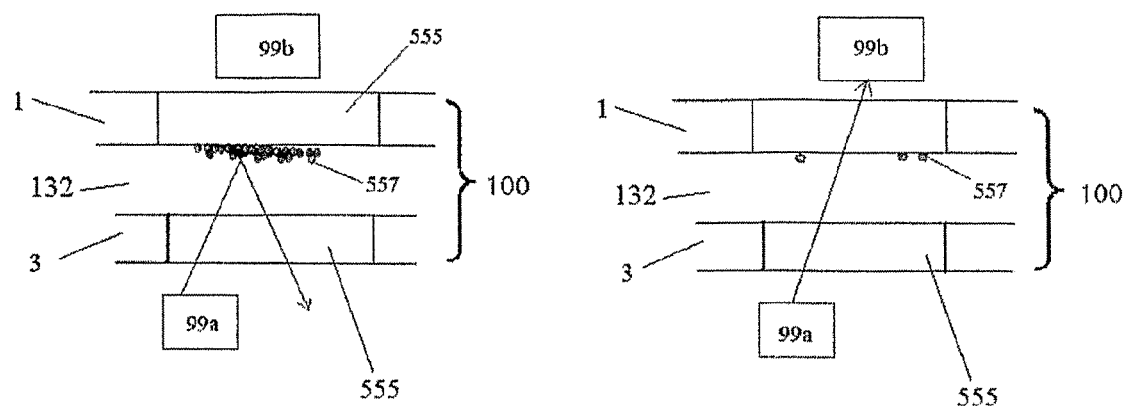
[Fig. 7]
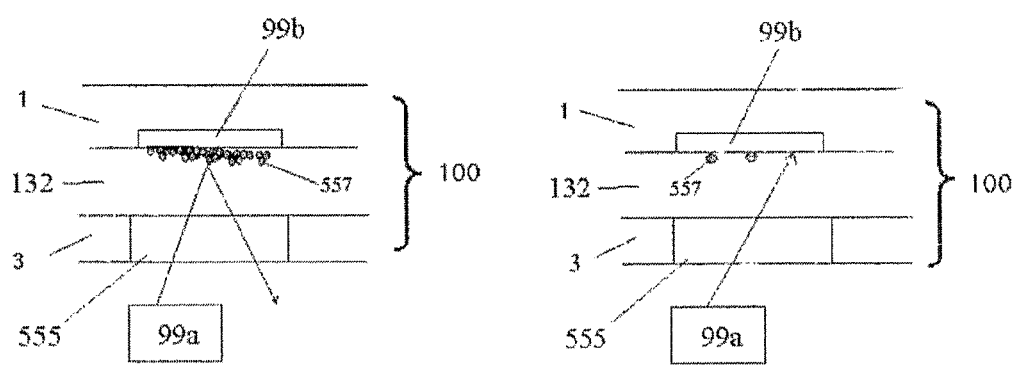

[Fig. 8]
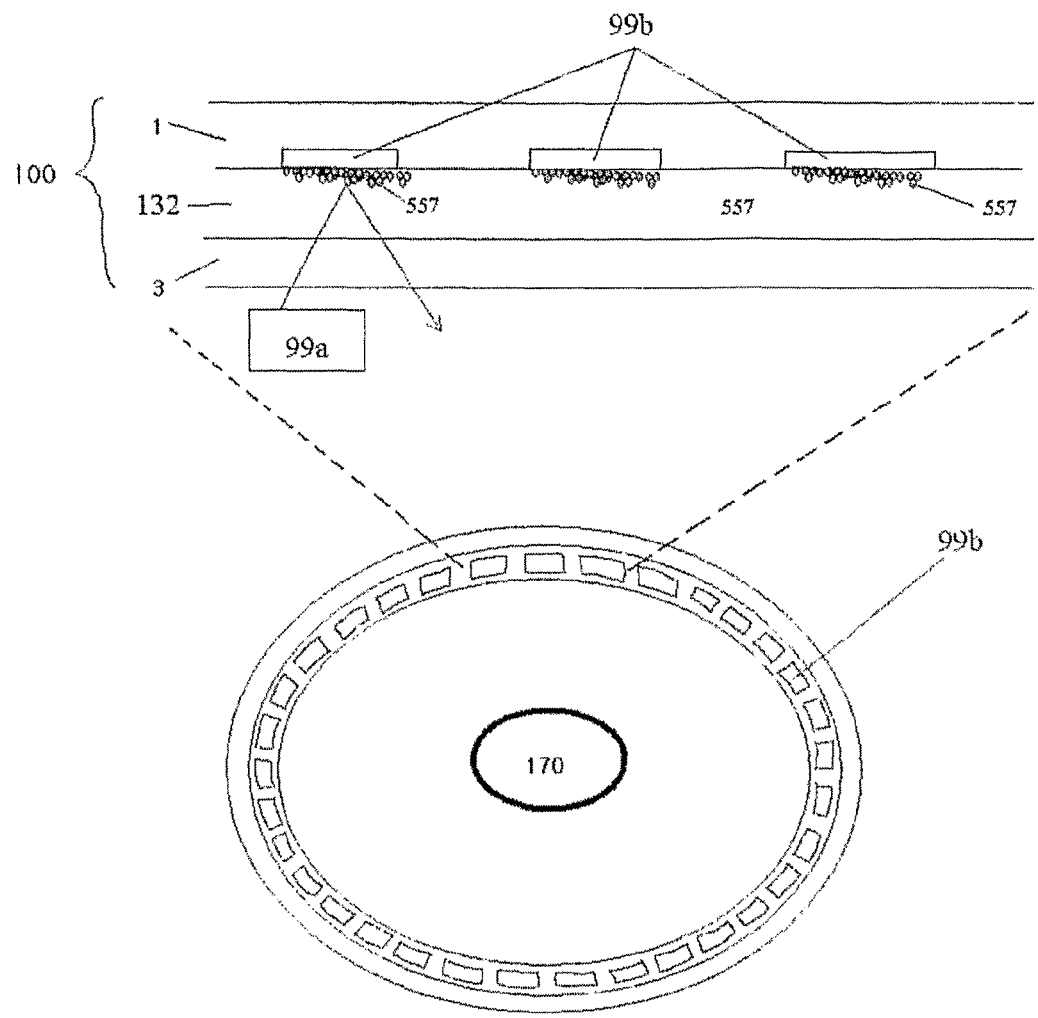
[Fig. 9]
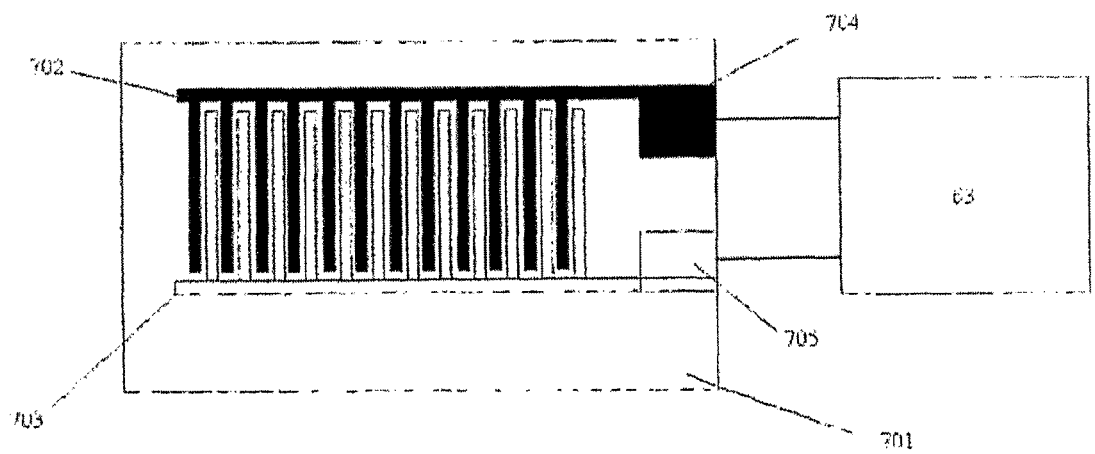

[Fig. 10]
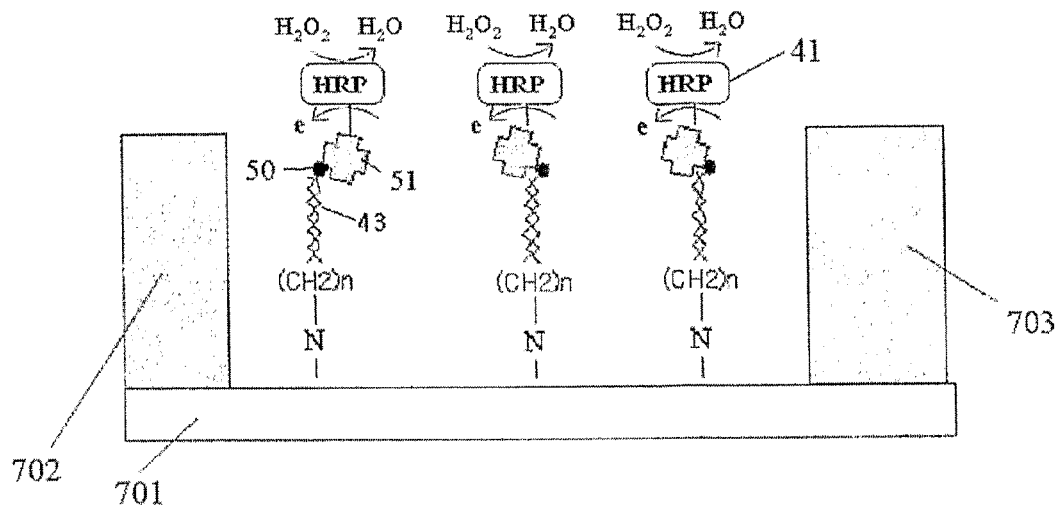
[Fig. 11]
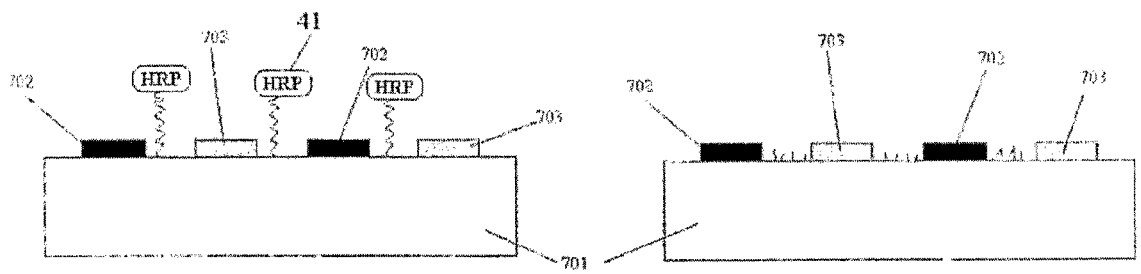
[Fig. 12]
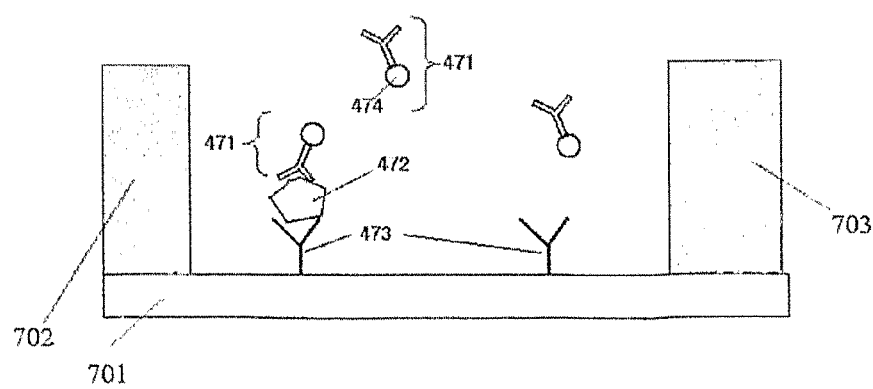

[Fig. 13]
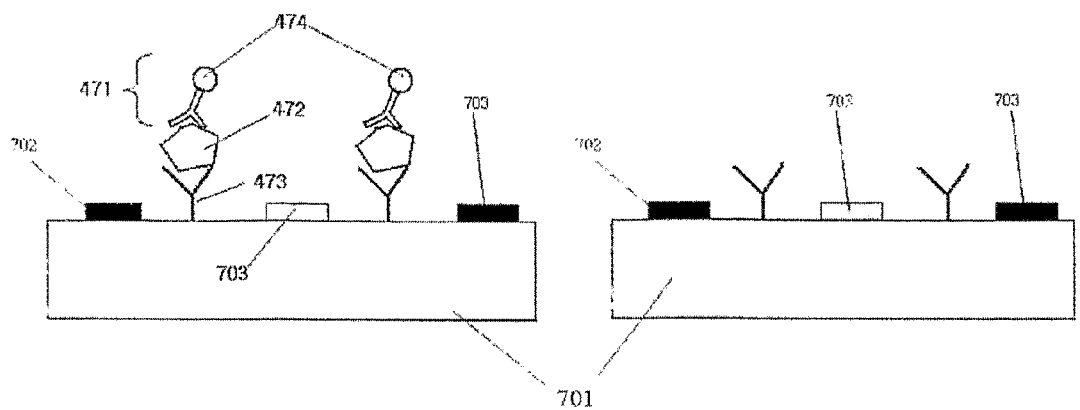
[Fig. 14]
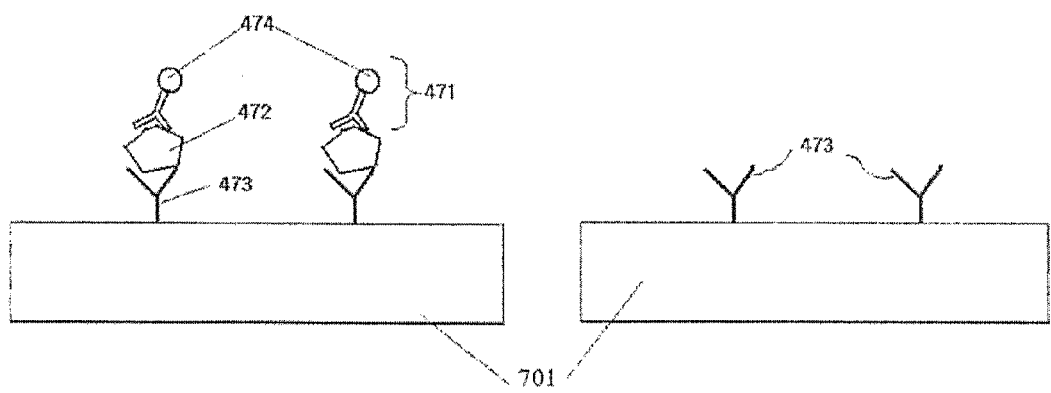

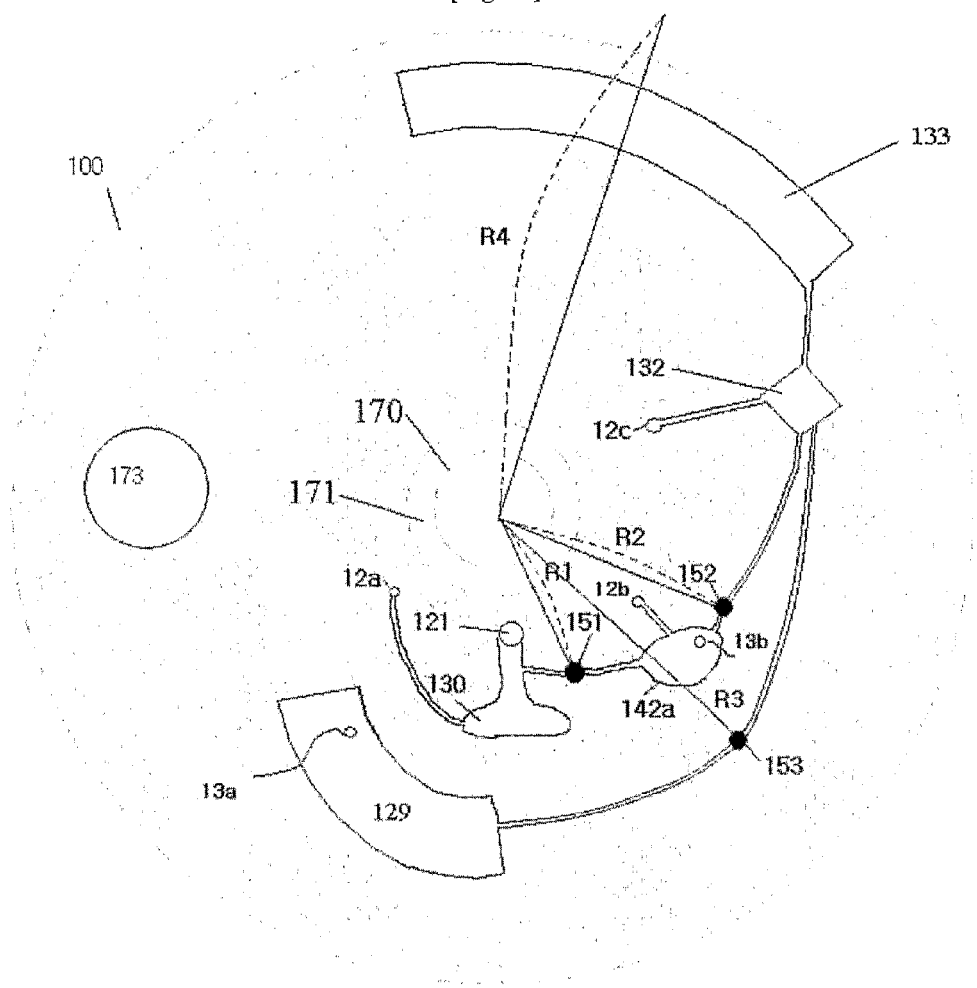
[Fig. 15]

[Fig. 16]
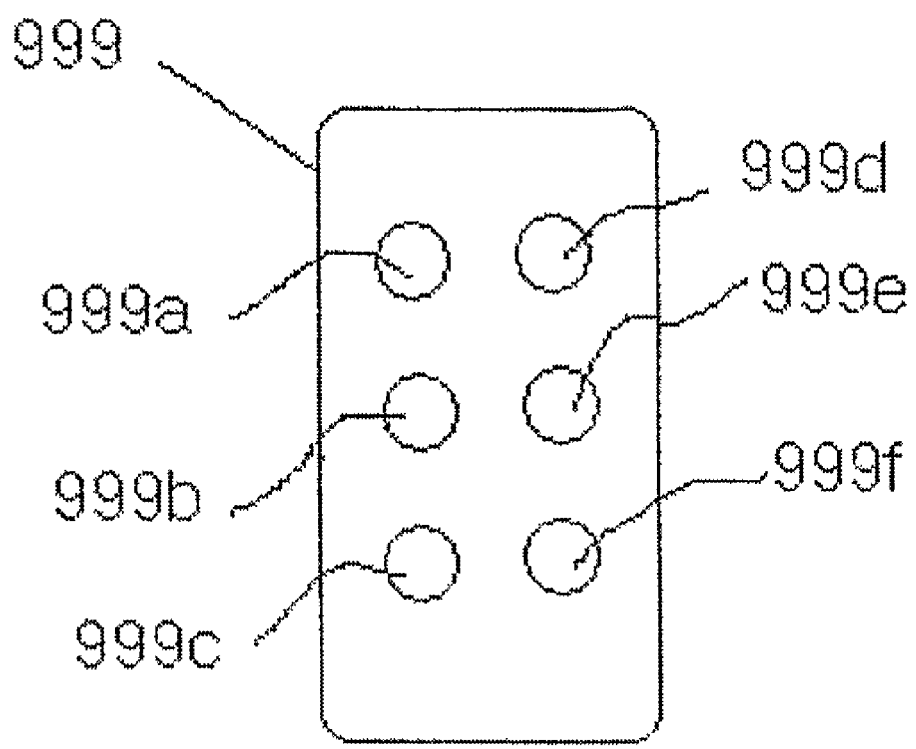

[Fig. 17]
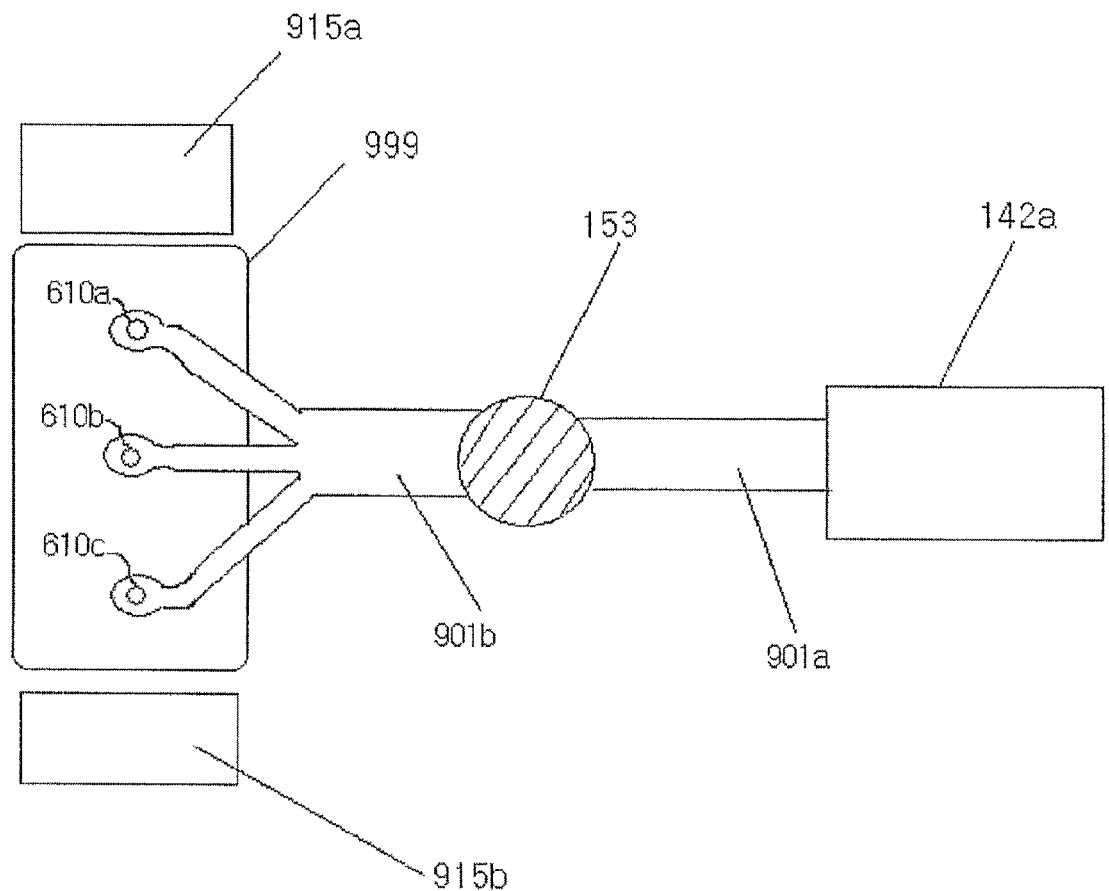
[Fig. 18]
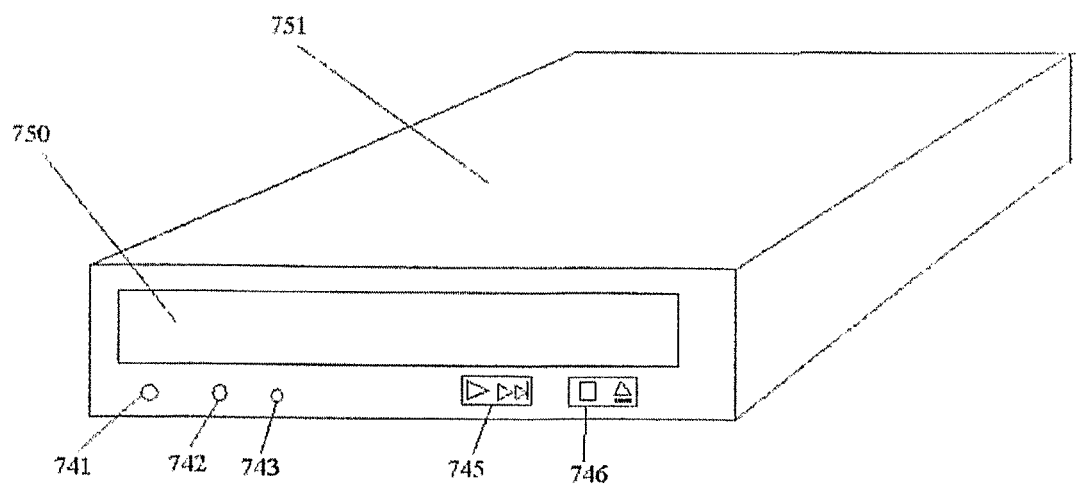

[Fig. 19]
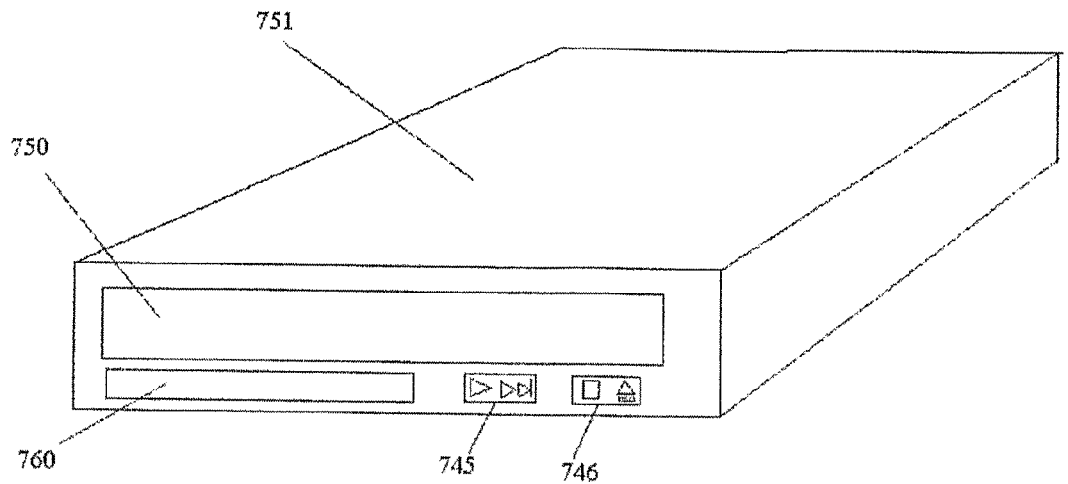
[Fig. 20]
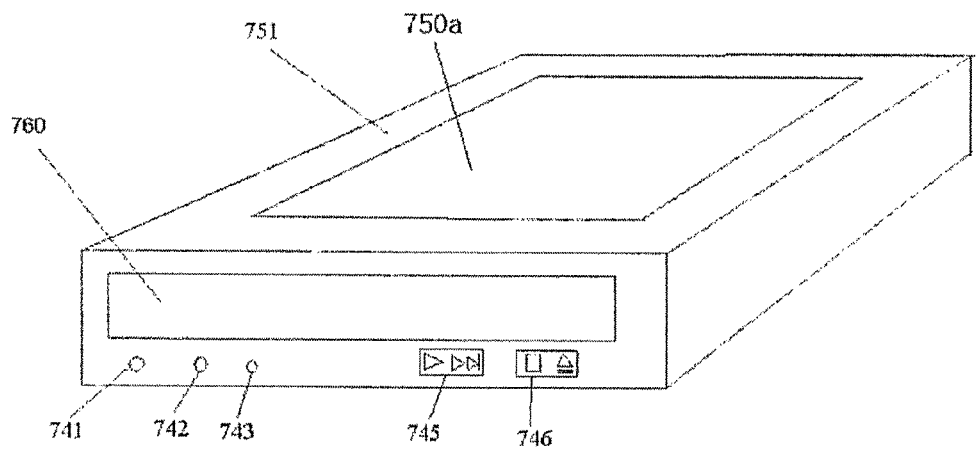
[Fig. 21]
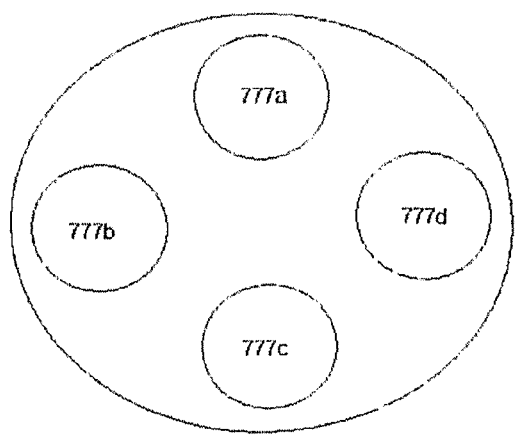

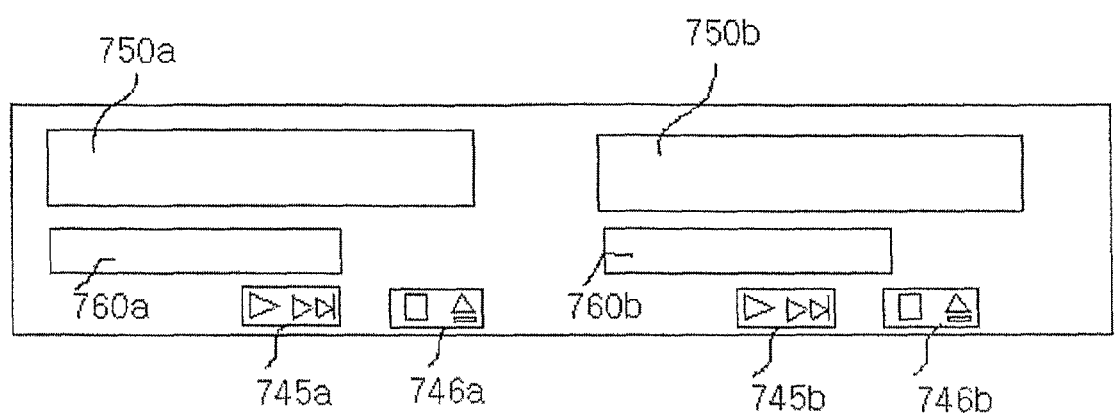
[Fig. 22]

DIGITAL BIO DISC (DBD), DBD DRIVER APPARATUS, AND ASSAY METHOD USING THE SAME

CROSS-REFERENCE TO RELATED APPLICATIONS

This application claims the benefit of PCT Application No. PCT/KR2006/001709, filed May 6, 2006, and Korean Application No. 10-2005-0038765, filed May 6, 2005 in the Korean Intellectual Property Office, the disclosures of which is incorporated herein by reference.

BACKGROUND

1. Field

One or more embodiments relates to a digital bio disc (DBD) including new valve control means and fluid movement system, a digital bio disc (DBD) driver apparatus, and an assay method using the same. More particularly, the present invention relates to a DBD with a lab-on-a-chip for various diagnostic assays, nucleic acid hybridization assays, or immunoassays, a DBD driver apparatus integrated with a controller for controlling the DBD and a general optical disc (CD or DVD), and an assay method using the same.

Hereafter, a digital bio disc and a digital bio disc driver apparatus are referred to as a "DBD" and a "DBD driver apparatus", respectively.

2. Description of the Related Art

An aspect of embodiment relates to a continued application of International Patent Application No. PCT/KR02/00126, which was filed 27 Jan. 2002 and claims the priority of Korean Patent Application No. 10-2001-0003956, filed 27 Jan. 2001, and International Patent Application No. PCT/KR02/01035, which was filed 31 May 2002 and claims the priority of Korean Patent Application No. 10-2001-0031284, filed 31 May 2001. International Patent Application No. PCT/KR02/00126 and its priority Korean application are entitled "Nucleic acid hybridization assay method and device using cleavage technique responsive to complementary double strand or single strand of nucleic acids or oligonucleotides", and International Patent Application No. PCT/KR02/01035 and its priority Korean application are entitled "Micro valve apparatus using microbead and method for controlling the same". The disclosures of the above previous applications are incorporated herein by reference in their entirety.

The nucleic acid hybridization assay method and device using a cleavage technique responsive to a complementary double strand or single strand of-nucleic acids are applicable to diverse quantitative or qualitative assay devices. In addition, the micro valve is an essential element to control the flow of fluid in a lab-on-a-chip.

The nucleic acid assay device may include a detector including an optical device, an electrochemical device, or a capacitance and impedance measurement device to detect or cleaved signal elements. The detected results can be digitized as computer executable software and provided through an established communications network, such as the Internet, to a patient or a doctor. In this manner, a remote diagnostic system ensuring convenience to both patient and doctor can be implemented based on the nucleic acid assay device. A capacitance and impedance measurement for the detector may include interdigitated array electrodes with cleavable signal elements, as disclosed in the previous application.

An aspect of the embodiment relates to a DBD including optical or non-optical bio-disc, a DBD apparatus for controlling the DBD and a general optical disc (CD or DVD), and an assay method using the same.

Most clinical diagnostic assay devices developed so far for the detection of small quantities of analytes in fluids are used in serial or parallel connection with multiple-sample preparation and automated reagent addition devices for the simultaneous analysis of numerous test samples with higher efficiency. Such automated reagent preparation devices and automated multiplex analyzers are often integrated into a single device.

Clinical laboratory analyzers of this type can accurately perform hundreds of assays using small quantities of samples and reagents in one hour automatically or semi-automatically. However, these analyzers are expensive and only centralized laboratories and hospitals can afford them. Such centralization necessitates sample transport to the laboratory or hospital and often precludes urgent or emergent analysis of time-critical samples.

Thus, to address these problems, there is an increasing need for clinical analyzers which are cheap and easy-to-handle for everyone, such as clinical analyzers suitable for use at the patient bedside of in the patient's home without dedicated detectors.

<Optical and Non-Optical Bio-Discs>

The standard compact disk is formed from a 12-cm polycarbonate substrate, a reflective metal layer, and a protective lacquer coating. DVD stands for digital video disk, a type of optical disk of the same size as the compact disk, but with significantly greater recording capacity.

The polycarbonate substrate is optical-quality clear polycarbonate. In a standard pressed CD or DVD, the data layer is part of the polycarbonate substrate, and the data are impressed as a series of pits by a stamper during injection molding. In the injection molding process, melted polycarbonate is injected into a mold under high pressure and cooled in a mirror image of the mold or stamper. As a result, reverse pits of the stamper are formed on the polycarbonate disk surface during mastering as binary data. The stamping master is typically glass.

Information written to general optical discs, such as audio CDs, game CDs, refractivity in their dye layer. In a common CD using a differential reflectivity detection method, indentations of pits are formed in the CD to a depth on the order of one-eighth to one-quarter of the wavelength of an incident laser beam. The indentations cause destructive interference in a reflected beam and correspond to bits having a "0" value. Flat areas of the CD reflect the incident laser beam toward a detector and correspond to bits having a "1" value.

U.S. Pat. No. 5,580,696 discloses materials of a dye layer for optical discs using refractivity-based data detection. An optical disk using the dye layer is rotated about a rotary shaft and scanned by laser to read data from the dye layer.

However, a general optical pickup for the above-described optical discs includes both a light emitting unit and a light receiving unit in a single module. In this structure, its optical traveling path is relatively long, and there is a poor sensitivity problem of the light receiving unit. In addition, laser scanning for information reading requires actuating the optical pickup to a predetermined location on an optical disc and rotating the optical disc. Furthermore, when such an optical disc read by laser scanning is applied to a bio-assay device, problems such as physical deformation of probes and inaccurate assay results occur. Therefore, it is impossible for a general optical pickup (CD or DVD reader) to read a bio-disc, which makes a new pickup device needed.

Various technologies regarding CD-based assay devices have been disclosed: "Optical confocal compact scanning optical microscope based on compact disc technology" (Applied Optics, Vol. 30, No. 10, 1991), "Gradient-index objectives for CD applications" (Applied Optics, Vol. 26, Issue 7, 1987), and "Miniature scanning optical microscope based on compact disc technology" (Proc. Soc. Photo-opt. instrument Eng. page 1139-1169, 1989).

Patents regarding CD-based assay devices include U.S. Pat. No. 4,279,862 entitled "Centrifugal photometric analyzer" (published on 21 Jul. 1981) and U.S. Pat. No. 4,141,954 entitled "Reaction tube assembly for automatic analyzer" (published on 27 Feb. 1979).

GB 1075800 (published on 12 Jul. 1967), entitled "Disc for centrifuge", discloses a device for flowing a sample fluid supplied via an inject hole of a disc over its surface by centrifugal force. EP 3335946 (published on 12 Apr. 1965), entitled "Separating disks for centrifuge", discloses an apparatus for separating fluid samples injected via an inject hole of a disc by inducing flow of the samples through channels or chambers formed in the disc by centrifugal force.

U.S. Pat. No. 4,311,039 (published on 19 Jan. 1982), entitled "Disc centrifuge photosedimentometer", discloses a disc type chemical assay device using centrifugal force and optical detection.

However, the above-listed conventional assay devices failed to ensure perfect automation in assay and diagnosis and are unsuitable for a lab-on-a-chip.

Unlike the conventional optical discs using differential reflection from physical pits or the refractivity in dye layers, a bio-disc according to an aspect of embodiment reads information using light transmission, capacitance and impedance measurements, or electrochemical detection, wherein the bio-disc includes chambers as fluid reservoirs and channels as flow paths. Such a bio-disc according to an aspect of embodiment is referred to as a "non-optical bio-disc", in contrast to the conventional "optical" bio-discs using the differential reflection of laser light scanned over the bio-disc. The conventional ones could not detect information using light transmission due to their structure which includes a reflective metal layer and a dye layer.

Common polycarbonate substrates can be modified to suit to bio-discs, which are thin film type assay devices, for detecting a small quantity of an analyte in a fluid sample for the diagnostic purpose. In this case, instead of pits and a dye layer, channels as fluid flow paths and chambers as buffer reservoirs are formed in a surface of a polycarbonate substrate through injection molding. In addition, micro valves for controlling fluid flow through the channel and flow rate and an electronic controlling method of the micro valves are needed.

In a DBD according to an aspect of embodiment, channels as fluid flow paths and chambers as buffer reservoirs may be formed in a silicon wafer using semiconductor manufacturing processes. Such a DBD according to an aspect of embodiment includes an electronic circuit integrated into the silicon wafer to control fluid flow and flow rate.

SUMMARY

Additional aspects and/or advantages will be set forth in part in the description which follows and, in part, will be apparent from the description, or may be learned by practice of the invention.

An aspect of the embodiment is to provide a bio optical pickup module (BOPM) device including both of the detection device for detecting the assay site, such as a light transmission type measuring device, an electro-chemical detection device, a capacitance and impedance measuring device, an image sensor, or a bio-pit detection device, and a general optical device (a CD reader or a DVD reader) in a module.

Hereinafter, one or more embodiments will be described more clearly as follows.

According to an aspect of the embodiment, there is provided a digital bio-disc (DBD) including: a sample inlet; chambers which reserve a buffer solution or a reaction solution; an assay site where bio materials are arrayed on a substrate; channels through which fluid flows between the sample inlet, the chambers, and the assay site; holes which connect the channels; and a plurality of valves which are used to open and close the holes, wherein the valve is constructed with a micro-bead, a permanent magnet disposed above the micro-bead and an moveable permanent magnet disposed under the micro-bead by which opening and closing of the valve is controlled, and wherein the valves have different radial distances from a center of the disc, provided that a portion of the valves which are opened at the same timing have the same radial distance.

The term "assay site" used throughout the specification is referred to as an "array chamber" having a meaning that bio materials are arrayed thereon, or a "hybridization chamber" or an "antigen-antibody reaction chamber" having a meaning that a specific binding reaction of two bio materials, a ligand-receptor reaction, a hybridization reaction, or an antigen-antibody reaction takes place therein.

In the DBD according to another embodiment, the valves have different radial distances from the center of the disc, and the valves can be independently opened and closed by using the later-described radially-movable permanent magnet. In addition, some valves which need to be opened and closed at the same timing have the same radial distance. In this case, the valves having the same radial distance can be opened at the same time by a later-described pulse value operation. In a case where a plurality of samples are injected and a plurality of analyses are performed, a case where a single sample is injected and a plurality of analyses are performed, or a case where a plurality of chambers are opened at the same time in a single analysis, several valves needed to be opened at the same time.

In the DBD according to an aspect of the embodiment, when the micro-bead is located under the hole, the valve is closed by an attractive force between the micro-bead and a film-like permanent magnet disposed above the micro-bead, and the valve is opened by an attractive force between the micro-bead and the moveable permanent magnet disposed under the micro-bead. When the micro-bead is located above the hole, the hole are opened and closed in a reverse arrangement. Namely, when the micro-bead is located above the hole, the hole is opened and closed (i) by a repulsive force instead of the attractive force or (ii) by a reverse arrangement of the magnets. The reverse arrangement of the magnets means that the film-like permanent magnet is fixedly disposed under the micro-bead, and a movable permanent magnet is disposed above the micro-bead, so that the hole of the value is opened and closed by an attractive force therebetween. If the disc is faced up and down, the top and bottom positions are changed. Therefore, the case (ii) is also included in the scope of the present invention.

When the micro-bead is located under the hole, since the film-like permanent magnet disposed above the micro-bead is not movable, the hole is always closed by the attractive force between the micro-bead and the film-like permanent magnet. Therefore, the hole of the DBD under distribution is always closed, so that it is possible to prevent liquid in the chamber from leaking.

In addition, when the micro-bead is located above the hole to open the hole by the repulsive force, since the film-like permanent magnet disposed above the micro-bead is not movable, the hole is always closed by the repulsive force between the micro-bead and the film-like permanent magnet. Therefore, the hole of the DBD under distribution is always closed, so that it is possible to prevent liquid in the chamber from leaking.

In the DBD according to an aspect of the embodiment, the hole of the DBD under distribution is always closed by the micro-bead and the permanent magnet disposed above the hole. Accordingly, it is possible to effectively prevent liquid in the chamber of the DBD under distribution from leaking. In a conventional bio-disc having a general valve, in order to prevent liquid in the chamber of the bid-disc under distribution, there is needed a sealed rubber tube, a capsule, or other additional device, or there is a need to solidify the liquid. However, in the DBD according to an aspect of the embodiment, the valve can be automatically closed.

In the DBD according to an aspect of the embodiment, the chamber may further include a venting hole and/or a reagent inlet. Here, the venting hole is used to vent air bubble generated in the channel or the chamber so as for the fluid to smoothly flow. The reagent inlet is used to inject the reagent required for a process of manufacturing the disc in the chamber.

In the DBD according to an aspect of the embodiment, the DBD may further include a vinyl cover or a protective vinyl which closes at least one of the sample inlet, the venting hole, and the reagent inlet. Since the vinyl cover has a tendency to adhere to the DBD, the vinyl cover can protect a surface of the DBD and close all the holes (the venting hole and the reagent inlet or optionally the sample inlet). Just before use of the DBD, the vinyl cover is uncovered from the DBD, so that the venting hole or the sample inlet can be opened and exposed. In addition, after a reagent is injected into the chamber, the reagent inlet can be sealed with a UV adhesive or a vinyl cover (protective cover) separate from the uncovered vinyl cover.

In the DBD according to an aspect of the embodiment, in addition to the chamber, the DBD may further include a balancing chamber or a balancing weight which makes a center of the disc weight-centered. If the DBD that rotates in a high speed is in a misalign center of mass, the DBD may be greatly shaken during high speed rotation. The balancing chamber or the balancing weight is needed to prevent the shaking of the DBD during high speed rotation.

In the DBD according to an aspect of the embodiment, the bio materials in the assay site may be immobilized on the substrate by immobilizing means if the immobilizing is needed. As an example of the immobilizing means, there is a magnetic bead assembled with the bio materials as a capture probe. When an external movable permanent magnet approaches the capture probe, the capture probe is fixed on the substrate by magnetic attraction. During a washing or detecting process, the immobilizing is needed. For example, during the washing process, the capture probe is fixed by a magnetic force. On the contrary, during a hybridization reaction or an antigen-antibody reaction, the capture probe is allowed to be in a floating or free state in order to activate the reaction. Alternatively, the aforementioned reactions may be activated by short forward and backward movements of the external movable permanent magnet in the vicinity of the assay site.

In the DBD according to an aspect of the embodiment, the micro-bead may have any material which can be moved by a magnetic field and any shape which can open and close the hole may be used as the micro-bead. Preferably, the micro-bead may be a film-like cylindrical magnet. The film-like cylindrical magnet may be coated with a cushion material. Alternatively, a film-like cushion material may be inserted between the micro-bead and the hole.

The cushion material may be a polymer having elasticity such a silicon rubber. Due to the cushion material, it is possible to more securely close the hole. When the film-like cushion material is inserted and assembled between the micro-bead and the hole, a thin film silicon rubber having a hole aligned with the hole is used, so that a production process can be simplified.

In the DBD according to an aspect of the embodiment, the movable permanent magnet may be mounted on a radially movable slider disposed under the DBD, so that the movable permanent magnet can be moved. Accordingly, the valves having different radial distances from the center of the disc can be addressed and controlled independently.

In the DBD according to an aspect of the embodiment, the fluid movement can be performed by a "pumping fluid movement" that a permanent magnet on the slider repeatedly performs rapid approaching and separating movements with respect to the center of the hole, with the rotation of the disc stopped.

For example, as shown in FIG. 3, repetition of the rapid approaching and separating movements of the permanent magnet 5a on the slider 211 with respect to the center of the hole causes up and down movements of the film-like cylindrical magnet. Due to the up and down movements of the film-like cylindrical magnet, a pumping force is generated and exerted on the fluid, so that the fluid can flow. The fluid movement by the pumping force is called a "pumping fluid movement". The pumping fluid movement can be useful in a later-described case where a centrifugal force cannot be used for the just-before valve of the assay site.

In the DBD according to an aspect of the embodiment, the pumping fluid movement may be performed after a "radial valve searching process" or an "azimuthal valve searching process" so as for the permanent magnet on the slider to precisely address the hole.

In the DBD according to an aspect of the embodiment, the fluid movement may be performed by a centrifugal force generated from rotation of the disc and a "pulse value operation" where the valves are repeatedly opened at the time that the holes of the valves are aligned with the permanent magnet disposed on the slider during rotation of the disc.

For example, as shown in FIG. 3, the fluid movement on the DBD 100 is performed by a centrifugal force generated from rotation of the DBD and a value operation where the valves are repeatedly opened at the time that the holes of the valves are aligned with the permanent magnet 5a disposed on the slider 211 during rotation of the DBD. In the present invention, the valve operation is called a "pulse valve operation". When such a high viscous fluid as serum is moved to next chamber by opening the hole, it may be difficult to stably move the high viscous fluid by using only a hydrophilic affinity of a hydrophilic channel and a capillary force. In this case, the fluid movement is formed by a centrifugal force in the pulse valve operation, so that it is possible to stably move the high viscous fluid.

In the DBD according to an aspect of the embodiment, the substrate in the assay site may be a porous membrane, a before channel of a just-before valve of the assay site is a hydrophobic channel, and an after channel of the just-before valve is a hydrophilic channel.

In the DBD according to an aspect of the embodiment, the porous membrane may be any membrane having a large number of pores. Preferably, the porous membrane may be one selected from a group consisting a NC (nitrocellulose) membrane, a nylon membrane, and aligned nanotubes. Due to the porous membrane according to the present invention, a surface area of the assay site can be increased, so that a large amount of bio material can be combined. Accordingly, it is possible to increase sensitivity.

In the DBD according to an aspect of the embodiment, the hydrophilic channel may be any channel where a hydrophilic material exists on a surface thereof. Preferably, the hydrophilic channel may be constructed by coating a surface of a hydrophobic channel with a hydrophilic acrylate, an ultra-hydrophilic poly (N-isopropylacrylamide) (PIPAAm) or an optical catalyst selected from a group consisting $ZrO_2$, $ZnO$, $Fe_2O_3$, and $TiO_2$ or by performing a surface modification on the hydrophobic channel with plasma. The optical catalyst may employ $ZrO_2$, $ZnO$, $Fe_2O_3$, $TiO_2$, or others. The $TiO_2$ is an affluent mineral in the earth. The $TiO_2$ is inexpensive, stable, and harmless to a human body. When a surface of the $TiO_2$ optical catalyst is illuminated with UV light, a contact angle with respect to water molecule is lowered down to 5 degrees, the water spread entirely over the surface, so that an ultra-hydrophilic phenomenon appears. Here, the term "hydrophilic" means that the contact angle between the surface of the substrate and water droplet spread on the surface thereof becomes less than 20 degrees. The term "ultra-hydrophilic" means that the contact angle becomes less than 10 degrees.

In the DBD according to an aspect of the embodiment, the hydrophilic channel is divided into at least one branch channel, and the hydrophilic channel is connected to the porous membrane through a hole provided to a distal end of the branch channel. In a case where there is a plurality of the branch channels, the branch channels may be located at the centers of the spots where the probes in the assay site are immobilized. When a size of the array (the number of spots) is 3×2, the number of the branch channel coated with a hydrophilic material may be three to six.

In the DBD according to an aspect of the embodiment, the assay site may have air holes disposed at the both sides of the assay site to dry the porous membrane. When the disc is rotated, air can be automatically absorbed or vented to or from the air holes disposed at both sides of the assay site, so that the porous membrane can be dried.

In the DBD according to an aspect of the embodiment, the fluid movement may be controlled by a centrifugal force due to rotation of the bio-disc and opening and closing of the valve. However, in a case where the substrate in the assay site is a porous membrane, a coupling of an analyzed material and a probe is formed by diffusion of a reaction solution into the porous membrane, and the diffusion rate is determined based on a pore size of the porous membrane. If the reaction solution is moved by the centrifugal force generated from the rotation of the disc, the diffusion rates changes, so that it is difficult to obtain consistent reproducibility of the reaction of the analyzed material and the probe. In order to solve the aforementioned problems, according to the present invention, the before channel of the just-before valve of the assay site is constructed with a hydrophobic channel, the after channel is constructed with a hydrophilic channel, and the fluid movement into the assay site is performed by the opening of the just before valve and hydrophilic affinity of the hydrophilic channel and the reaction solution without using a centrifugal force. Since most of reaction solutions are hydrophilic, the reaction solution is remained in the hydrophobic chamber and channel before the opening of the just-before valve, and the reaction solution can flow into the assay site through the hydrophilic channel after the opening of the valve.

In the DBD according to an aspect of the embodiment, the body of the DBD is constructed with an upper substrate, an intermediate substrate, and a lower substrate, and these substrates are adhered and assembled by using ultrasonic fusing, UV adhesive, or double-sided tape to form a single body.

In the DBD according to the present invention, the bio material is at least one selected from DNA, oligo-nucleotide, RNA, PNA, ligand, receptor, antigen, antibody, and protein.

The chamber of the DBD according to an aspect of embodiment may include at least one selected from the group consisting of: a preparation chamber for preparing a DNA sample from blood, cells, or RNA; a PCR chamber for amplifying the DNA sample through a polymerase chain reaction (PCR); a hybridization chamber in which assay and diagnostic probes are arrayed on the substrate for hybridization with the amplified DNA from the PCR; and a trash chamber for collecting wastes generated from washing.

The preparation chamber of the DBD according to an aspect of embodiment may reserve a lysis buffer solution used to destruct a cell and extract a DNA through lysis and particles or ferromagnetic beads having affinity to the extracted DNA. The particles may be silica or micro-bead coated with a DNA binding protein.

The preparation chamber may reserve only the buffer solution used to destruct the cell and extract the DNA without using the particles or ferromagnetic beads so as to prepare the DNA sample by using a centrifugal force generated from rotation of the bio-disc. More specifically, (1) cell membrane components including lipid is destructed by the lysis buffer solution, and the protein and the nucleic acid are dissolved. (2) When ethyl alcohol (ethanol) is applied, the DNA and RNA are extracted as a white precipitate. (3) When centrifugal separation is performed to obtain the DNA precipitated by ethanol, the DNA is collected at the end of the preparation chamber. After the valve of the preparation chamber toward the trash chamber is opened, the top layer solution is flowed into the trash chamber by rotation of the disc, so that the cell debris is separated and removed. Next, a dilution buffer is injected into the preparation chamber to be mixed with the DNA so as to increase a total volume of the DNA. The process (3) repeats about three times. (4) The connection valve toward the PCR chamber is opened, so that the DNA is moved into the PCR chamber.

The DBD according to an aspect of embodiment may include a plurality of the PCR chambers. In this case, each PCR chamber may reserve one type or several types of primer. Alternatively, all the PCR chambers may reserve the same type of primer.

Alternatively, the chamber of the DBD according to an aspect of embodiment may include at least one chamber selected from the group consisting of: a preparation chamber for preparing a serum sample, an antigen, or an antibody from blood or cells; an antigen-antibody reaction chamber in which immuno probes are arrayed on the substrate for an antigen-antibody reaction with the prepared antigen or antibody; and a trash chamber for collecting waste generated from washing. The serum sample may be a blood plasma sample.

In the DBD according to an aspect of embodiment, the immuno probe array is constructed by arraying tumor markers on a substrate. More preferably, the immuno probe array may be constructed by arraying at least one tumor marker selected from AFP, PSA, CEA, CA19-9, CA125, and CA15-3 on the substrate.

In the DBD according to an aspect of embodiment, the immuno probe may be at lease one selected from myoglobin, CK-MB, and Troponin I (Tn 1) as a cardiac infraction marker and GS (Glutamine Synthetase) as an Alzheimer's diseases marker.

Alternatively, the chamber of the DBD according to an aspect of embodiment may include at least one chamber selected from the group consisting of: a preparation chamber for preparing a serum or hemoglobin sample from blood; an antigen-antibody reaction chamber where anti-HbA1c antibody or glucose antibody is arrayed on the assay site to react with an antigen, glucose, or HbA1c in the prepared sample; and a trash chamber for collecting wastes generated from washing. In this case, an amount of HbA1c or glucose is measured by an image sensor for detecting a color of the assay site, and an amount of hemoglobin is measured by an intensity of coloring of hemoglobin, so that diabetes can be diagnosed.

In the DBD according to an aspect of embodiment, the preparation chamber may further contain an RBC (Red blood Cell) lysis buffer solution used to destruct red blood cells and extract hemoglobin.

In the preparation chamber of the DBD according to an aspect of embodiment, a serum sample may be prepared by using a filter. Preferably, the serum sample may be prepared by using a centrifugal force generated by rotation of the disc. In this case, the preparation chamber may have a shape of a bottle having a depth to the outer circumference and a channel at a bottle neck separated by a predetermined height from the bottom to be connected to a next chamber. Therefore, a blood clot is collected on the bottom of the bottle, so that only the remaining serum can be moved to the next chamber.

In the DBD according to an aspect of embodiment, the preparation chamber may be a chamber having a shape of a conical beaker, a flask, or a test tube in order to facilitate separating serum in centrifugal separation and a channel at a neck portion in order to be connected to a next chamber. In this case, due to a centrifugal force, a blood clot is collected in a circumferential outer space of the chamber (on a bottom of the conical beaker or the flask), so that the serum can be easily separated.

In the DBD according to an aspect of embodiment, the DBD may further include a label chamber for reserving a labeled antibody. Here, the label may be a coloring particle linked with an antibody. The label may be gold, latex, a fluorescent marker, an enzyme, and a radioactive isotope. In a case where the label is enzyme, the DBD may further include a substrate chamber for reserving a substrate which reacts with the enzyme.

In the DBD according to an aspect of embodiment, the DBD may further include an impedance measuring device in the preparation chamber. The impedance measuring device may be an interdigitated array. The preparation chamber must be injected with a suitable amount of blood (or sample). A user must not operate the bio-disc without inserting blood. Alternatively, in order to prevent operation without blood, an image sensor is used to observe the preparation chamber just before the start of the operation of the bio-disc and check whether or not a suitable amount of sample is injected into the preparation chamber.

In the DBD according to an aspect of embodiment, the assay site may include an immuno assay sector and a nucleic acid probe assay sector arranged in an angular or radial direction to enable an immuno assay and a nucleic acid probe assay to be performed concurrently.

In the DBD according to an aspect of embodiment, the assay site may be detected by a detection device coupled with a transforming device, and the detection device may include a light transmission type measuring device, an electro-chemical detection device, a capacitance and impedance measuring device, an image sensor, or a bio-pit detection device. The DBD according to an aspect of embodiment includes a non-optical bio-disc or an optical bio-disc.

In the DBD according to an aspect of embodiment, the light transmission type detection device may include: a laser device (light transmitting unit) which emits a laser beam onto a confined signal element and a released signal element; and an optical detector (light receiving unit) which detects a differential light transmission signal between the signal elements. The term "confined signal element" means that a signal such as a label is confined to the probe. The term "released signal element" means that a signal such as a label is released or cleaved from the probe. In this case, the light transmitting unit or the light transmitting and receiving units may be disposed outside the DBD, for example, on the detector on the slider.

In the DBD according to an aspect of embodiment, at least one optical detector (light receiving unit) may be arrayed and integrated along a circumference of the DBD to correspond to each assay site. In this case, a smaller distance between the optical detector and the corresponding assay site offers higher detection sensitivity. Alternatively, at least one laser device (light transmitting unit) and at least one optical detector (light receiving unit) may be arrayed and integrated along a circumference of the DBD to correspond to each assay site. In this case, the assay site can be detected from the assay site in a non-scanning manner without rotation of the disc. In the DBD according to an aspect of embodiment, in a case where the confined signal element of the assay site is labeled with a fluorescent marker or a radioactive isotope, the detection of the confined signal element excited by the laser generation device can be performed by an image sensor.

In the DBD according to an aspect of embodiment, the electro-chemical detection device and the capacitance and impedance measuring device may include: interdigitated array electrodes disposed on the substrate of the assay site; and a HRP (Horse Radish Peroxidase) and/or enzyme and/or a metal micro-sphere attached to the end of confined signal elements. In this case, the electro-chemical detection device and the capacitance and impedance measuring device using the interdigitated array electrodes may be implemented by voltage generation, current detection, frequency generation, or oxidation reduction reaction.

In the DBD according to an aspect of embodiment, the DBD may further include an RF IC which controls the voltage generation, current detection, frequency generation, or oxidation reduction reaction of the electro-chemical detection device or the capacitance impedance measuring device using the interdigitated array electrodes and performs detection and an induction coil and a condenser for supplying electricity to the RF IC, wherein a result of the detection is transmitted to an external central controller, a storage unit, or an input output device in a wireless manner.

In the DBD according to an aspect of embodiment, the DBD may further include a non-contact interface with a DBD driver which controls the voltage generation, current detection, frequency generation, or oxidation reduction reaction of the electro-chemical detection device or the capacitance and impedance measuring device using the interdigitated array electrodes and performs detection. The non-contact interface according to an aspect of embodiment may be a spring pin.

In the DBD according to an aspect of embodiment, the interdigitated array electrodes may be constructed by coating a surface of a porous membrane with a conductive material. The conductive material may be gold or copper, and more preferably, gold.

In the DBD according to an aspect of embodiment, the assay site may be constructed by arraying an antigen, an antibody, a DNA capture probe, or oligo-nucleotide on a porous membrane. Alternatively, the assay site may be constructed by coating a surface of interdigitated electrodes on the porous membrane and arraying an antigen, an antibody, a DNA capture probe, or oligo-nucleotide between the interdigitated electrodes. The porous membrane may be NC (Nitrocellulose), nylon membrane, or nanotube.

In the DBD according to an aspect of embodiment, the image sensor picks up an image of a label (coloring particle) linked with the probe and obtains image information.

In the DBD according to an aspect of embodiment, the coloring particle is excited by a laser generating device, and the excited image information on the assay site is obtained by the image sensor.

The image sensor may be constructed with a CCD (charge coupled Device) sensor or a COMS sensor with or without a fluorescent filter to pick up an image of the label (coloring particle) linked with the probe in the assay site. In a case where reference numeral 103b in FIG. 3 is an image sensor, the image sensor may be an image sensor mounted on BOPM such as a CIS sensor or other image sensor having a short focusing distance. Therefore, the image sensor mounted on the BOPM can detect the assay site on the disc at a near position thereof. On the other hand, in a case where reference numeral 144 in FIG. 5 is an image sensor, the image sensor may be an image sensor mounted on a main board 140, and after a florescent label is excited by a laser device 107, a florescent light is detected by the image sensor, that the florescent label of the assay site on the disc is measured. In this case, a fluorescent filter or various lenses may be disposed in front of the image sensor. In this case, the focusing distance of the image sensor 144 is too long to obtain a suitable focusing distance by using the BOPM. Therefore, the image sensor 144 is disposed on the main board 140 which is distant from the disc.

In the DBD according to an aspect of embodiment, the bio-pit detection device that detects bio-pits generated from the confined signal element and the released signal element may be any one of an STM (Scanning Tunneling Microscope), an AFM (Atomic Force Microscope), a cantilever AFM, an MFM (Magnetic Force Microscope), and an SNOM (Scanning Near-field Optical Microscope).

In 1981, an STM (Scanning Tunneling Microscope) as a first type of an SPM (Scanning Probe Microscope) was contrived by Binning, et. al. The STM is based on a quantum mechanically tunneling effect of electrons in microscopic regions. When a probe approaches a sample very closely and a small voltage of form millivolts to volts is applied across the probe and the sample, quantum mechanical electron tunneling effect that a tunneling current of from tens of picoamperes to nanoamperes flows occurs. The measurement of the tunneling current is used to analyze characteristics of the sample. The STM have well known by the ordinarily skilled in the related art.

In comparison with the STM using a current between the probe and the sample, the AFM uses an atomic force between the probe and the sample to measure physical properties of a micro structure of the sample. In 198, the AFM was contrived by Binning, Quate, and Gerber. At first, the AFT utilized bending of a cantilever formed by the atomic force based on the principle of STM to measure physical properties. Recently, the optical lever technique has been generally used. Namely, light of the laser reflected on a tip of the probe is changed according to the bending or displacement of the cantilever, and changed light beams are detected by different optical diodes. Under the assumption that the displacement of the cantilever satisfies Hook's law, a force between the tip and the sample is calculated. Recently, a technique of depositing piezo-resistive thin film on the cantilever and measuring the bending of the cantilever based on change in resistance of the thin film without using an optical system has been used. The technique is also well known by the ordinarily skilled in the related art.

An optical microscope generally used has a limitation in that the optical microscope has a resolution according to a wavelength of light. According to Rayleigh Criterion, two objects can be discriminated when a maximum of Airy function of the one object is located at least at a minimum of Airy function of the other object. Therefore, a resolution of an optical microscope is always larger than a half of a wavelength of light. For example, an optical microscope using visible light having a wavelength of 488 nm has a resolution of 250 nm. However, in 1928, Synge proposed a method of controlling a distance between a sample and an aperture to overcome the limitation of Rayleigh resolution. When the distance between the aperture and the sample is reduced down to a half of a radius of the aperture, light is incident on the sample before the light is scattered. Therefore, the resolution can be increased by controlling the radius of the aperture and the distance between the aperture and the sample. The principle is used to contrive an SNOM (Scanning Near-field Optical Microscope) that is also well known by the ordinarily skilled in the related art.

In addition, there is an MFM (Magnetic Force Microscope) that is most widely used to research and observe magnetic properties of substances. In the MFM, a silicon probe coated with a ferromagnetic material is used to measure a force between a magnetic field generated from a sample and a magnetic moment of the probe. According to the MFM, while the cantilever is vibrated at a natural frequency of about 100 kHz by a piezo device, scanning is performed in order to obtain a higher resolution. The MFM can measure magnetic properties of the sample by using change in natural frequency due to interaction between the sample and the magnetized probe as well as the aforementioned bending of the cantilever. The MFM is also well known by the ordinarily skilled in the related art.

In the DBD according to an aspect of embodiment, the DBD may further includes a memory or other storage means or RF IC for storing a protocol of the DBD, assay interpretive algorithms, standard control values for analysis, positional information on analysis sites, bioinformatics information, self-diagnostics, DBD driver software, educational information for patients on clinical assays, a variety of web sites and links enabling a patient to communicate with a doctor or hospital at a remote location based on his/her diagnosis result, or encrypted personal information.

The DBD according to an aspect of embodiment may further include an RF IC which transmits a detection result of the assay site obtained by the detection device to an external central controller, a storage device, or an input output device through an RF interface.

In the DBD according to an aspect of embodiment, the RF IC may includes a condenser for storing a sufficient amount of electricity generated from the induction coil embedded in the DBD through an external RF wave.

According to another aspect of an aspect of embodiment, there is provided a DBD driver apparatus including: a turn-table on which the aforementioned DBD is mounted; a spindle motor which rotates the DBD; a slider which includes a detector device for detecting the assay site in the DBD and a permanent magnet for controlling opening and closing of the valves in the DBD; a slide motor which controls moving of the slider; a central controller which controls whole components of the DBD driver; and a body which supports the DBD driver.

In the DBD driver apparatus according to an aspect of embodiment, the detector device is one selected from a light transmittance measuring device, an electro-chemical detection device, a capacitance and impedance measuring device, an image sensor, and a bio-pit detection device.

In case of the light transmittance measuring device, only the light transmitting unit or both of the light transmitting and receiving units may be disposed on the slider. In case of the an electro-chemical detection device and the capacitance impedance measuring device, an interdigitated array electrode is disposed on the assay side in the DBD, and only a control device and a transforming device are disposed on the slider.

The DBD driver apparatus according to an aspect of embodiment may further include a detection device coupled with a transforming device, wherein the detection device may include an image sensor and a laser generation device for detecting a confined signal element of the assay site labeled with a fluorescent marker or radioactive isotope.

The DBD driver apparatus according to an aspect of embodiment may further include a detection device coupled with a transforming device, wherein the detection device may include an image sensor and a light emitting diode (LED) for detecting a confined signal element of the assay site labeled with a coloring particle.

In the DBD driver apparatus according to an aspect of embodiment, the image sensor may be a line image sensor for sensing a light intensity in units of a pixel.

In the DBD driver apparatus according to an aspect of embodiment, the line image sensor may be a linear sensor array or a CIS (Contact Image Sensor).

In the DBD driver apparatus according to an aspect of embodiment, the line image sensor may further include a light emitting diode (LED) for illumination with a wavelength of from 500 nm to 800 nm and an optical lens which are disposed in the vicinity of the line image sensor.

In the DBD driver apparatus according to an aspect of embodiment, the line image sensor may be moved on the slider to obtain two-dimensional image information of the assay site.

The DBD driver apparatus according to an aspect of embodiment may further include an optical pickup device (a CD reader or a DVD reader) for reading a general optical disc (for example, an audio CD, a CR-R, a game CF, and a DVD).

In the DBD driver apparatus according to an aspect of embodiment, preferably the slider is provided with a bio optical pickup module (BOPM) device including the detection device for detecting the assay site and a general optical device (a CD reader or a DVD reader) in a module.

In the DBD driver apparatus according to an aspect of embodiment, preferably the bio optical pickup module (BOPM) device and the movable permanent magnet are designed to be disposed on the slider, and moving thereof is controlled by a slide motor.

In the DBD driver apparatus according to an aspect of embodiment, the slider is connected to the slide motor through a worm gear so that the moving thereof is controlled.

In the DBD driver apparatus according to an aspect of embodiment, the bio optical pickup module (BOPM) device may further include contact interface means for supplying a control signal to the assay site in the DBD and reading a detection signal from the assay site in the DBD. In the DBD driver apparatus according to an aspect of embodiment, the contact interface means is used for a light transmittance detection device of a DBD having a light receiving unit, or an electro-chemical measuring device or a capacitance and impedance measuring device of a DBD having an interdigitated array.

In the DBD driver apparatus according to an aspect of embodiment, the fluid movement in the DBD can be performed by a "pumping movement" that a permanent magnet on the slider repeatedly performs rapid approaching and separating movements with respect to the center of the hole, with the rotation of the disc stopped.

In the DBD driver apparatus according to an aspect of embodiment, the pumping fluid movement may be performed after a "radial valve searching process" or an "azimuthal valve searching process".

The radial valve searching process is performed by movement of the slider, and the azimuthal valve searching process is performed by rotation of the disc. For example, the azimuthal valve searching process is performed by repetition of short rotations of the disc due to a small torque. During several times of the short rotations, when the micro-bead located at the center of the hole is aligned with the movable permanent magnet disposed under the hole, the short rotation of the disc is stopped by a strong attraction therebetween, so that the disc is stopped at the associated position. Preferably, an angle of the short rotation is in range of from 10 degrees to 20 degrees. In case of 20 degrees, the azimuthal valve searching process is completed by 18 times of the short-rotations. Alternatively, a permanent magnet may be disposed at an azimuthal position on an upper portion of the DBD, so that the disc can be stopped at a predetermined azimuthal position by using the azimuthal valve searching process. During several times of the short rotations, when the permanent magnet disposed above the DBD is aligned with the movable permanent magnet disposed under the DBD, the short rotation of the disc is stopped by a strong attraction therebetween, so that the disc is stopped at the associated position. This is called an "azimuthal valve searching process".

In the DBD driver apparatus according to an aspect of embodiment, the fluid movement in the DBD may be performed by a centrifugal force generated from rotation of the disc and a "pulse value operation" where the valves are repeatedly opened at the time that the holes of the valves are aligned with the permanent magnet disposed on the slider during rotation of the disc.

In the DBD driver apparatus according to an aspect of embodiment, a circuit board on which a central controller and a storage device or an input output device are disposed is engaged with the DBD driver body, and the central controller rotates and stops the spindle motor at the time of rotating and stopping the DBD and rotates and stops the slide motor for controlling moving of a detector device for detection of the assay site in the DBD and a permanent magnet for control of opening and closing of the valves in the DBD.

In the DBD driver apparatus according to an aspect of embodiment, the input output device may be a USB (Universal Serial Bus) device or a device according to IEEE-1394, ATAPI or Internet communication standard.

The DBD driver apparatus according to an aspect of embodiment may further include an RF wave generation unit for supplying power to the RF IC on the DBD. The wave generated by the RF wave generation unit is induced to the inductive coil embedded in the RF IC of the DBD according to Fleming's law so that a sufficient amount of electricity is stored in a condenser.

The DBD driver apparatus according to an aspect of embodiment may further include a bio-disc detection unit for determining whether a currently loaded disc is a DBD or a general optical disc selected from among an audio CD, a CD-R, a game CD, and a DVD.

In the DBD driver apparatus according to an aspect of embodiment, an optical pickup device may read a groove pattern or a data pattern at a particular area on a surface of the DBD to allow the central controller to recognize that a disc currently loaded on the DBD driver is a DBD.

In the DBD driver apparatus according to an aspect of embodiment, a central controller may determine whether a currently loaded disc is a DBD or a general optical disc selected from among an audio CD, a CD-R, a game CD, and a DVD; transmit information read from the general optical disc using the optical pickup to a storage or output unit, transmit information to be written to the optical pickup device, or output various control signals required for read/write if the currently loaded disc is determined to be a general optical disc; and transmit various control signals for control of the DBD to the bio optical pickup (BOPM) device or the RF IC if the currently loaded disc is determined to be a DBD.

In the DBD driver apparatus according to an aspect of embodiment, at the time of loading the DBD, a new loading of the DBD is transmitted to the central controller in a wireless manner through a non-contact interface or an RF IC on the DBD, so that the central controller recognizes that the disc loaded on the DBD driver is the DBD.

The DBD driver apparatus according to an aspect of embodiment may send an eject message or a warning message to a user if a DBD into which a sample has not be injected is loaded.

In the DBD driver apparatus according to an aspect of embodiment, when an eject (unloading) or a stop command is input to the DBD driver apparatus during assay or diagnosis, the DBD driver apparatus sends a warning message or requests a user's password while continuing assay and diagnosis. If the user enters the correct password, the DBD driver apparatus stops the assay or diagnosis and ejects the DBD.

The DBD driver apparatus according to an aspect of embodiment, may further include a memory storing information on how many times a DBD has been used, its validation period, and kinds of diseases which it can diagnose, so as to provide a user with the stored information on the DBD or the availability of the DBD whenever the DBD is loaded.

The DBD driver apparatus according to an aspect of embodiment may further include statistic software and storage means for managing a history of the detection results of the assay site and provides periodical diagnosis information to a user. This is useful when the probe in the assay site is a tumor marker.

The DBD driver apparatus according to an aspect of embodiment may further include software for determining a negative, positive, or dangerous state and calculating an associated value by detecting signal intensity by using the detection device. For example, the image sensor may measure an intensity of coloring by analyzing image information on a coloring particle.

The DBD driver apparatus according to an aspect of embodiment may include: a play and search button and a stop button for general optical discs; and a light emitting diode (LED) indicating that a DBD has been loaded.

In the DBD driver apparatus according to an aspect of embodiment, includes a liquid crystal display or a monitor to display the status of progress in main processes performed in the DBD such as a sample preparation process, PCR, a hybridization, and an antigen-antibody reaction in percentages or as a bar graph or a pie graph.

In the DBD driver apparatus according to an aspect of embodiment, the body which supports the DBD driver may allow DBD top loading or DBD front loading.

In the DBD driver apparatus according to an aspect of embodiment, the DBD driver may have a plurality of turntables so as to load a plurality of the DBDs in one time.

In the DBD driver apparatus according to an aspect of embodiment, the DBD driver may be a double deck driver so as to load the DBD for diagnosis and a DVD disc for movies.

In the DBD driver apparatus according to an aspect of embodiment, the DBD driver may be a combo driver having a DBD driver at one side and a VCR (Video Cassette Recorder) at the other side. Accordingly, a movie can be seen during the diagnosis.

According to another aspect of an aspect of embodiment, there is provided a nucleic acid assay method using the DBD according to an aspect of embodiment, the method including: preparing a DNA sample from blood, cells, or RNA; amplifying the prepared DNA through polymerase chain reaction (PCR); hybridizing amplified DNA products from the PCR with the assay and diagnostic probe arrayed on the assay site; and detecting a result of hybridization reaction in the assay site by using a detection device coupled with a transforming device, wherein the detection device includes a light transmission type measuring device, an electro-chemical detection device, a capacitance and impedance measuring device, an image sensor, or a bio-pit detection device.

In the nucleic acid assay method according to an aspect of embodiment, the preparing of the DNA sample may includes: injecting blood via a sample inlet into the preparation chamber; performing incubation in the preparation chamber to allow particles or ferromagnetic beads in the preparation chamber to attract DNA extracted through lysis; fixing the particles or ferromagnetic beads and slowly rotating the DBD to wash out and flow the cell debris into the trash chamber; and separating the DNA from the particles or ferromagnetic beads or resuspending the DNA in a resuspension buffer.

The preparing of the DNA sample may include: injecting the blood through a sample inlet disposed in the preparation chamber; and separating the DNA extracted through cell lysis by centrifugation using rotation of the DBD. In an example, sodium dodecyl sulfate (SDS) may be injected as a reagent for cell lysis. The SDS is a surfactant such as a detergent. By doing so, membrane components including lipid is destructed, and protein and nucleic acid are dissolved. In an example, phenol may be injected as a reagent for deforming the protein. After that, by centrifugal separation, the nucleic acid including DNA and RNA can be obtained.

In the nucleic acid assay method according to an aspect of embodiment, the amplifying of the prepared DNA sample through PCR may includes: rotating the DBD to allow the prepared DNA sample to flow into the PCR chamber; and repeating a PCR cycle several times using a heater and a thermo-sensor installed in the PCR chamber to amplify the DNA sample.

The nucleic acid assay method according to an aspect of embodiment may further include, after the PRC process: rotating the DBD to allow a DNAse to flow into the PCR chamber; and heating the PCR chamber at a high temperature to deactivate the DNAse and form single-stranded DNA fragments (denaturing process).

In the nucleic acid assay method according to an aspect of embodiment, each PCR chamber may include a heater which is controlled independently from the heaters of the other PCR chambers (in independent incubation time intervals) to form the DNA fragments having different lengths.

According to another aspect of an aspect of embodiment, there is provided an immuno assay method using the DBD according to an aspect of embodiment, the method including: rotating the DBD at high speed to extract serum or an antigen from blood; introducing the extracted antigen into a label chamber and performing incubation in the chamber for 1-2 minutes to bind the antigen to labeled antibodies and form a label-antigen complex; moving the label-antigen complex into the assay site; and performing cultivation in the DBD in a stationary state to induce an antigen-antibody reaction between the label-antigen complex and the capture antibodies; and adding a washing buffer and washing the assay site; and optionally detecting the assay site by using a detection device coupled with a transforming device, wherein the detection device includes a light transmission type measuring device, an electro-chemical detection device, a capacitance and impedance measuring device, an image sensor, or a bio-pit detection device.

According to another aspect of an aspect of embodiment, there is provided a immuno assay method using the DBD according to an aspect of embodiment for diabetes diagnosis or blood sugar level analysis, the method including: preparing serum or hemoglobin from blood; introducing the prepared antigen into a label chamber and performing incubation in the chamber for 1-2 minutes to bind the antigen to labeled antibodies and form a label-antigen complex; moving the label-antigen complex into the assay site; and performing cultivation in the DBD in a stationary state to induce an antigen-antibody reaction between the label-antigen complex and the capture antibodies; and adding a washing buffer and washing the assay site; and optionally detecting the assay site by using a detection device coupled with a transforming device, wherein the detection device includes a light transmission type measuring device, an electro-chemical detection device, a capacitance and impedance measuring device, an image sensor, or a bio-pit detection device.

The nucleic acid assay or immuno assay method according to an aspect of embodiment may further include, before the detecting of the assay site, cleaning and drying the assay site.

The nucleic acid assay or immuno assay method according to an aspect of embodiment may further include a warbling mixing process in the performing of the incubation, the cultivation, the hybridizing, or the antigen-antibody reaction.

In the nucleic acid assay or immuno assay method according to an aspect of embodiment, in the moving of the label-antigen complex or the DNA into the assay site, the label-antigen complex or the DNA is allow to flow in to a porous membrane of the assay site by opening a just-before valve of the assay site and using a hydrophilic affinity of a hydrophilic channel without a centrifugal force.

The nucleic acid assay or immuno assay method according to an aspect of embodiment may further include, after the performing cultivation to induce an antigen-antibody reaction or hybridization reaction between the label-antigen complex or the DNA and the capture antibodies on the porous membrane, drying the porous membrane by a high speed rotation of the disc.

The nucleic acid assay or immuno assay method according to an aspect of embodiment may further include, after the drying, moving a washing buffer by opening a just-before valve of the assay site and using a hydrophilic affinity of a hydrophilic channel and cleaning the assay site by using the washing buffer.

The nucleic acid assay or immuno assay method according to an aspect of embodiment may further include, after the cleaning, drying the porous membrane by a high speed rotation of the disc.

In the nucleic acid assay or immuno assay method according to an aspect of embodiment, the method may further includes a remote diagnosis step where the diagnostic data based on the result of the detection are displayed on a computer monitor, the diagnostic result together with a questionnaire sheet is optionally automatically or manually transmitted through the Internet to a specialist at a remote location, and the patient waits for a prescription from the specialist.

BRIEF DESCRIPTION OF THE DRAWINGS

The above and other objects, features and other advantages of an aspect of embodiment will be more clearly understood from the following detailed description taken in conjunction with the accompanying drawings, in which;

FIGS. 1 and 2 are cross-sectional views showing a valve device using a micro-bead disposed in a DBD;

FIG. 3 is a view showing a DBD and a DBD driver for controlling the DBD according to an embodiment of an aspect of embodiment;

FIG. 4 is a bio optical pickup module (BOPM) according to an embodiment of an aspect of embodiment;

FIG. 5 is a view showing a DBD driver apparatus according to an embodiment of an aspect of embodiment;

FIGS. 6 to 8 are views showing various embodiments using an optical measuring device;

FIGS. 9 to 14 is a view showing a detection method using an electro-chemical detection device, a capacitance measuring device, an impedance measuring device, or an image sensor according to an embodiment of an aspect of embodiment;

FIGS. 15 to 17 are views showing a DBD and an assay site used for an immuno assay reaction analysis; and FIGS. 18 to 22 are views showing an outer appearance of a DBD driver apparatus according to an aspect of embodiment.

DETAILED DESCRIPTION OF THE EMBODIMENTS

Reference will now be made in detail to the embodiments, examples of which are illustrated in the accompanying drawings, wherein like reference numerals refer to the like elements throughout. The embodiments are described below to explain an aspect of embodiment by referring to the figures.

A DBD according to an aspect of embodiment includes a valve which controls fluid flow or the flow rate in a lab-on-a-chip integrated in the DBD. The valve opens or closes a channel formed in the DBD using a microbead that is movable by the magnetic force generated by a permanent magnet and a movable permanent magnet disposed on the top and bottom surface of the DBD. International Patent Application No. PCT/KR02/01035 filed 31 May 2002 and its priority Korean Application No. 10-2001-0031284 filed 31 May 2002, which are entitled "Micro valve apparatus using microbead and method for controlling the same", can be referred to for the detailed structure of the valve.

In exemplary embodiments of the DBD according to an aspect of embodiment, the microbead may include, for example, a magnetic ball, ferroelectric particles, paramagnetic particles, diamagnetic particles, a stainless steel ball. Alternatively, the microbead may be made of a solid metal, plastic, or glass bead. When the microbead is made of a plastic or glass bead, the microbead is further coated with a metal or a cushion material such as silicone rubber. Solid metals for the microbead may be metal alloys. The microbead may be charged. In which case, instead of permanent magnets, electrode plates may be arranged on the top and bottom surfaces of the DBD. The microbead is charged and moved in the direction in which a voltage is applied to the electrode plates, to open or close a hole connecting channels in the lab-on-a-chip. The microbead has a diameter of 1 um-1 mm, preferably, 100 um-500 um. When the diameter of the microbead is larger, the hole can be opened or plugged with higher reliability due to an increase in the contact area between the hole and the microbead. The microbead may be a spherical permanent magnet or a film-like cylindrical or rectangular permanent magnet. The film-like permanent magnet may have a thickness of, preferably, 0.1 mm-0.5 mm. The electromagnet may be a wound wire having a diameter of, preferably, 0.01 mm-0.5 mm. Preferably, instead of the coating of microbead, a film-like cushion material may be inserted between the micro-bead and the hole.

FIGS. 1 and 2 are sectional views of a DBD showing a valve apparatus therein using a permanent magnetic microbead 70a above which a permanent magnet 4a is disposed and under which a movable permanent magnet 5a is disposed.

As shown in FIGS. 1 and 2, a DBD 100 includes an upper substrate 1, an intermediate substrate 2, and a lower substrate 3. Channels as flow paths, chambers as buffer reservoirs, and holes connecting the channels are formed in each of the upper, intermediate, and lower substrates 1, 2, and 3 by injection molding. Next, the upper, intermediate, and lower substrates 1, 2, and 3 are bound together to form a body of the DBD 100.

FIG. 1 illustrates a state where a hole 10 is plugged by a permanent magnetic microbead 70a to block a channel 16a. FIG. 2 illustrates a state where the permanent magnetic microbead 70a is removed from the hole 10 to interconnect the channel 16a. To plug the hole 10 with the permanent magnetic microbead 70a and block the channel 16a, as shown in FIG. 1, a movable permanent magnet 5a is removed from bottom surface (the center of the hole) of the DBD. In this case, the hole 10 is plugged by an attractive force between the micro-bead and a film-like permanent magnet 4a disposed above the micro-bead. In contrast, to open the hole 10 and interconnect the channel 16a, as shown in FIG. 2, the movable permanent magnet 5a is moved to bottom surface (the center of the hole) of the DBD.

Preferred example of the lower magnet 5a is a movable permanent magnet mounted on a radially movable slider disposed under the DBD. Since the DBD 100 according to an aspect of embodiment includes the channel 16a, which is relatively narrow, as a fluid path, a ventilating hole 12 is formed in the upper substrate 1 to reduce the air pressure and allow a fluid to smoothly flow through the channel FIG. 3 illustrates a DBD 100, in which chambers as various assay buffer reservoirs and places for various reactions, channels as flow paths of a fluid sample and buffers, and valve apparatuses for controlling the opening and closing of the channels are integrated to form a lab-on-a-chip, and bio driver apparatus for controlling the DBD 100.

Suitable materials for the DBD 100 according to an aspect of embodiment include plastics, polymethylmethacrylate (PMMA), glass, mica, silica, any material for semiconductor wafers, etc. However, among these materials, plastics are most preferred for economical reasons and the convenience of processing. Suitable examples of plastics include polypropylenes, polyacrylates, polyvinyl alcohols, polyethylenes, polymethylmethacrylates, COC (Cyclic Olefin Copolymer) and polycarbonates, with COC, polypropylenes and polycarbonates being preferred and polycarbonates being more preferred.

As described above with reference to FIGS. 1 and 2, the DBD 100 includes the upper substrate 1, the intermediate substrate 2, and the lower substrate 3. Channels as flow paths, chambers as buffer reservoirs, and holes connecting the channels are formed in each of the upper, intermediate, and lower substrates 1, 2, and 3 by injection molding. Next, the upper, intermediate, and lower substrates 1, 2, and 3 are bound together to form a body of the DBD 100.

International Patent Application No. PCT/KR02/01035 filed 31 May 2002 and its priority Korean Patent Application No. 10-2001-0031284 filed 31 May 2001, which are entitled "Micro valve apparatus using microbead and method for controlling the same", can be referred to for the detailed structure of the valve.

The DBD 100 is built of the upper substrate 1, the intermediate substrate 2, and the lower substrate 3 stacked upon one another. Permanent magnetic microbeads 70a, 70b, and 70c are individually moved up and down by the magnetic force generated by respective upper permanent magnets 4a, 4b, 4c and lower movable permanent magnet 5a to close and open holes connecting channels. In FIG. 3, reference numeral 120 denotes a pipette or syringe for sample injection, reference numeral 121 denotes a sample inlet, and reference numeral 170 denotes a disk hole. Reference numeral 130 denotes a preparation chamber for preparing a DNA sample directly from blood or cells or from RNA through reverse transcription (RT) or for preparing a serum sample from blood, reference numeral 131 denotes a PCR chamber for polymerase chain reaction (PCR), and reference numeral 132 denotes a chamber for hybridization or antigen-antibody reaction, which is an assay site with capture probes for analyzing and diagnosing amplified DNA products from the PCR or with immuno arrays immobilized thereon. Reference numeral 133 denotes a trash chamber for collecting wastes generated during washing. Reference numeral 211 denotes a slider on which the movable permanent magnet 5a is mounted, the slider is connected with and controlled by slide motor 109. Reference numeral 140 denotes a chamber for reserving a buffer for PCR, and reference numerals 141, 142, and 143 denote chambers for reserving various enzymes required for hybridization.

Opening and closing of the valve apparatuses at the start and ending points of time of each of the processes (preparation, PCR, hybridization, antigen-antibody reaction, and washing) are controlled by approaching/separating movement of the movable permanent magnet 5a mounted on slider 211. Fluid flow in the DBD 100 is induced by the centrifugal force generated as it is rotated.

Reference numeral 103a denotes an optical pickup device (a CD reader or a DVD reader) for reading a general optical disc (for example, an audio CD, a CR-R, a game CF, and a DVD). Reference numeral 103b denotes a detection device such as a light transmission type measuring device, an electro-chemical detection device, a capacitance and impedance measuring device, an image sensor, or a bio-pit detection device. The optical pickup device 103a and the detection device 103b is combined in a module to provide a bio optical pickup module (BOPM) device 103.

In a case where reference numeral 103b in FIG. 3 is an image sensor, the image sensor may be an image sensor mounted on BOPM such as a CIS sensor or other image sensor having a short focusing distance. In this case, the line image sensor may further include a light emitting diode (LED) for illumination with a wavelength of from 500 nm to 800 nm and an optical lens which are disposed in the vicinity of the line image sensor. The BOPM device 103 including the line image sensor may be moved on the slider 211 to obtain two-dimensional image information of the assay site.

In FIG. 3, the bio optical pickup module (BOPM) device 103 may further include contact interface means 240 and 241 for supplying a control signal to the assay site in the DBD 100 and reading a detection signal from the assay site in the DBD 100. The contact interface means 240 and 241 is used for an light transmittance detection device of a DBD having a light receiving unit, or an electro-chemical measuring device or a capacitance and impedance measuring device of a DBD having an interdigitated array to control the voltage generation, current detection, frequency generation, or oxidation reduction reaction thereof.

In FIG. 3, the central control system 101 may generate a control signal for the detection device 103b such as a light transmission type measuring device, an electro-chemical detection device, a capacitance and impedance measuring device, an image sensor, or a bio-pit detection device in order to read the assay site 132 in the DBD 100.

Reference numeral 110b denotes a flexible cable to connect various control signals needed for the BOPM device 103 and contact interface means 240 and 241 on the slider 211 and is connected with the central control system 101 via a wafer or harness 110a.

Reference numeral 181 denotes a turntable on which the DBD 100 or a general optical disc, such as an audio CD, a CD-R, a game CD, or a DVD, is loaded and which engages the disc hole 170 of the DBD 100 or a general optical disc. In disc 200 is fixed to the turntable 181, and the DBD 100 is loaded on the turntable 181 in a top loading or front loading type.

As described above, the memory embedded RFIC card 188 of the DBD 100 stores a protocol of the lab-on-chip, assay interpretive algorithms, standard control values for analysis, positional information on analysis sites, bioinformatics information, self-diagnostics, and the like. The RFIC card 188 may include bio-driver software, educational information for patients on clinical assays and may be adapted for users. The RFIC card 188 may include a variety of web sites and links, for example, a web site enabling a patient to communicate with a doctor or hospital based on his/her diagnosis result, and encrypted personal information to prevent unauthorized user assess.

A preferred example of the RFIC card 188 is a RAM or ROM embedded smart card. The information stored in the RFIC card 188 may be wirelessly transmitted to the central control system 101 to allow for remote analysis and diagnosis and encryption for personal information security. Reference numeral 110 denotes a RF wave generation unit for supplying power to the RF IC 188 on the DBD.

In FIG. 3, the RF IC 188 may control the voltage generation, current detection, frequency generation, or oxidation reduction reaction of the electro-chemical detection device or the capacitance impedance measuring device using the interdigitated array electrodes and transmit a result of the detection to an external central controller 101, a storage unit, or an input output device 111 in a wireless manner.

Reference numerals 240a and 241a denote connecting nodes for the contact interface means 240 and 241 in order to read the assay site on the DBD 100. The connecting nodes 240a and 241a are coated with a conductive material and connected with the contact interface means 240 and 241 to provide a control signal to the assay site in the DBD 100.

FIG. 4 illustrates an embodiment of slider 211 on which the BOPM device 103, the movable permanent magnet 5a and the contact interface means 240, 241 are disposed. The slider 211 is connected to the slide motor 109 through a worm gear 109a and its counter part 109b so that the moving thereof is controlled.

The slider 211 is moved in sliding on slide arms 108a and 108b as a guide. The slide arms 108a and 108b are connected with the body of the DBD driver through screws 110a, 110b, 110c, and 110d. Reference numeral 110b denotes a flexible cable to connect various control signals needed for the BOPM device 103 and contact interface means 240 and 241 on the slider 211 and is connected with the central control system via a wafer or harness 110a. Reference numeral 181 denotes a turntable which is rotated by the spindle motor.

FIG. 5 illustrates an embodiment of a bio-driver apparatus for controlling the DBD 100 which is loaded on the turntable 181.

In FIG. 5, the contact interface means 240 and 241 on the slider 211 supply a control signal to the assay site in the DBD 100 and read a detection signal from the assay site in the DBD 100. One end of the contact interface means 240 and 241 is fixed in the slider 211 and the other end thereof is fitted into the connecting nodes 240a and 241a, which are coated with a conductive material, when reading the assay site.

Reference numeral 300 denotes a body for supporting the DBD driver. A circuit board 140 on which a central controller 101 and a storage device or an input output device 111 are disposed is engaged with the DBD driver body 300 as a base. The central controller 101 controls the spindle motor 102 for rotating and stopping of the DBD 100 and the slide motor 109 for moving of the BOPM device 103 mounted on the slider, as well as the permanent magnet 5a for opening and closing of the valves in the DBD. On opening the valve, the permanent magnet 5a approaches the center of the hole in the DBD so closely that can exert an attractive force to the film-like cylindrical magnet 70a in the DBD effectively.

The central control system 101 determines whether a disc currently loaded into the bio-driver apparatus is a general optical disc, for example, an audio CD, CD-R, a game CD, or a DVD, or a non-optical DBD. If the currently loaded disc is determined to be a general optical disc, the central control system 101 transmits information read from the optical disc using the optical pickup 103a to the storage or input output unit 111 or transmits information to be written to the optical pickup 103a and controls the operation of the optical disc using read/write control signals. If the currently loaded disc is determined to be a DBD, the central control system 101 sends various control signals for controlling the lab-on-a-chip of the DBD to the RFIC card 188 of the DBD 100 via the non-contact interface 106. The RFIC card 188 of the DBD 200 transmits the received control signals to the lab-on-a-chip of the DBD 100.

The DBD driver apparatus according to an aspect of embodiment may further include a bio-disc detection unit for determining whether a disc currently loaded on the DBD driver apparatus is a bio-disc (DBD) or a general optical disc selected from among an audio CD, a CD-R, a game CD, and a DVD.

In the DBD driver apparatus according to an aspect of embodiment, an optical pickup device may read a groove pattern or a data pattern at a particular area on a surface of the DBD 100 to allow the central control system 101 to recognize that a disc currently loaded on the DBD driver is a DBD. Alternatively, when a DBD is loaded, a RFIC card 188 on the DBD may wirelessly transmit the loading information to the central control system 101 to allow the central control system to recognize that a disc currently loaded on the DBD driver is a DBD.

The result of a detection from the array chamber (assay site) 132 of the DBD 100, which is obtained by a detector including an optical device, an electrochemical device, a capacitance and impedance measurement device, an image sensor, or a bio-pit detection device, is transmitted to the central control system 101 or the storage or input output unit 111 via the flexible cable 110b connected to the slider 211.

Alternatively, the result of a detection from the array chamber (assay site) 132 of the DBD 100, which is obtained by a detector including an optical device, an electrochemical device, or a capacitance and impedance measurement device, is transmitted to the central control system 101 or the storage or input output unit 111 via the RFIC card 188 embedded in the DBD 100. Alternatively, an image sensor 144 arranged on the PCB 140 transmits the results of a detection from the assay site 132 by the image sensor to the central control system 101 or the storage or input output unit 111. Reference numeral 107 denotes a laser generation device which excites the confined signal element of the assay site labeled with a fluorescent marker or a radioactive isotope. The detection of the confined signal element excited by the laser generation device can be performed by the image sensor 144.

FIG. 6 illustrates an embodiment of the optical assay detectors which detect analyte-specific signals from the assay site 132 using light transmission method.

The left sectional view of FIG. 6 shows a state where numerous signal elements 557 are immobilized on the surface of the upper substrate 1 of the DBD 100 (confined signal element), and the right sectional view of FIG. 6 shows a state where only a few signal elements 557 remain on the upper substrate 1 after cleavage reaction (released signal element).

In the embodiment of FIG. 6, the optical array detectors 99a and 99b are implemented with a laser device (light transmitting unit), which emits a laser beam onto the cleavable signal elements 557, and a photodetector (light receiving unit), which detects a differential light transmission signal. A transparent opening 555 is further formed for higher sensitivity of the photodetector 99b.

FIG. 7 illustrates a modification of the optical array detectors of FIG. 6 based on light transmission, in which the photodetector 99b is integrated into the upper substrate 1. In this embodiment, a plurality of photodetectors 99b is arrayed one-to-one corresponding to a plurality of assay sites. This arrangement of the plurality of photodetectors 99b is distinguished from a modular light transmission and reception unit used in the general optical pickup 103, the modular light transmission and reception unit causing a low sensitivity problem at a receiving site due to its longer reflection path.

FIG. 8 illustrates an embodiment of a DBD with a plurality of photodetectors 99b arrayed along its outer perimeter region. As the DBD is rotated, individual analyte sites in the DBD are sequentially detected by the corresponding photodetectors 99b.

FIGS. 9 through 14 illustrate examples of electrochemical detectors, capacitance and impedance measurement devices, image sensors, or bio-pit detection devices for detecting analyte-specific signals from the assay site 132 of the DBD 100. Some of the electrochemical detectors or capacitance impedance measurement devices illustrated in FIGS. 9 through 14 are implemented with interdigitated array electrodes 702 and 703 arranged on a substrate 701 and a metal microsphere 40 or horse radish peroxidase (HRP) 41 attached as signal responsive moiety to each end of probes on the substrate 701. Some of the electrochemical detectors or capacitance impedance measurement devices are based on antigen-antibody reaction mainly used for immunochromatography. In the DBD according to an aspect of embodiment, the porous membrane may be any membrane having a large number of pores. The substrate 701 may be preferably a porous membrane coated with interdigitated array electrodes and the porous membrane may be one selected from NC (nitrocellulose) membrane, a nylon membrane, and aligned nanotubes.

FIG. 9 illustrates an example of an electrochemical detector or a capacitance and impedance measurement device with interdigitated array electrodes 702 and 703.

The controller 63 applies an AC signal having a given bandwidth to two input ports 704 and 705 of the respective interdigitated array electrodes 702 and 703 to measure the frequency response characteristics of assay sites and then the capacitance and impedance of the assay sites from the frequency response characteristics. Alternatively, the controller 63 may be able to measure a voltage or a current induced as a result of the reduction/oxidation (REDOX) of analytes by HRP in $H_2O_2$ solution, thereby enabling electrochemical detection of assay sites. For the detailed structure of such a capacitance and impedance measurement device using interdigitated array electrodes, International Patent Application No. PCT/KR02/00126 filed 27 Jan. 2002 and its priority Korean Patent Application No. 10-2001-0003956 filed 27 Jan. 2001, which are entitled "Nucleic acid hybridization assay method and device using cleavage technique responsive to complementary double strand or single strand of nucleic acids or oligonucleotides," can be referred to.

FIGS. 10 and 11 illustrate an example of an electrochemical detector or a capacitance and impedance measurement device for detecting analyte-specific signals from the assay site 132 of the DBD 100. The electrochemical detector or the capacitance and impedance measurement device of FIGS. 10 and 11 is implemented with the interdigitated array electrodes 702 and 703 arranged on the substrate 701 and HRP 41 attached as signal responsive moiety to each cleavable signal element immobilized as a probe on the substrate 701. Electrons are generated as a result of successive REDOX reactions by the HRP 41 and induce a current and a voltage across the interdigitated array electrodes 702 and 703. The sensitivity of the interdigitated array electrodes 702 and 703 becomes higher with more digits.

The assay site 132 of the DBD 100 is manufactured by aminating the surface of the substrate 701, forming a nonreactive monolayer, for example, of alkane chains the aminated surface of the substrate 701, and immobilizing cleavable signal elements labeled with biotin 50, wherein the nonreactive layer is for preventing direct contact of the cleavable signal elements with the substrate 701.

After sample injection, cleavable signal elements which are not hybridized with a sample remain as single strands are cleaved and removed through washing. Meanwhile, cleavable signal elements which are hybridized with the sample and form double strands 43 remain after the cleavage and washing processes. Next, streptavidin-labeled HRP is injected to bind the streptavidin 51 to the biotin labeled to the signal elements.

Next, a series of REDOX reactions of the signal elements are caused by the HRP in $H_2O_2$ solution to induce a voltage and a current across the interdigitated array electrodes 702 and 703. The controller 63 measures the voltage and the current across the interdigitated array electrodes 702 and 703. In this way, a differential electrochemical signal between the confined and cleaved (released) signal elements can be detected.

The left sectional view of FIG. 11 shows a state where cleavable signal elements remain on the DBD 100, so that the signal elements in the assay site 132 are highly likely to be oxidized and reduced by the HRP in solution. The right sectional view of FIG. 11 shows a state where most cleavable signal elements are cleaved and removed through washing so that REDOX reaction is unlikely to occur. A differential electrochemical signal between the two states is detected.

FIG. 12 illustrates another example of an electrochemical detector or a capacitance and impedance measurement device for detecting analyte-specific signals from the assay site 132 of the DBD 100. The electrochemical detector or the capacitance and impedance measurement device of FIG. 12 is implemented with the interdigitated array electrodes 702 and 703 arranged on the substrate 701 and a labeled antibody 471 which forms a label-antigen complex with a target sample (analyte or antigen) to be assayed. The label-antigen complex is applied to an assay site 312 in which capture antibodies 473 are immobilized on the substrate 701. The electrochemical detector or the capacitance and impedance measurement device of FIG. 12 is based on antigen-antibody reaction between the label-antigen complex and the capture body 473. The labeled antibody 471 is labeled with coloring moiety 474 made of, preferably, gold, latex, a fluorescent material, an enzyme, or a radioactive isotope.

When the label-antigen complex reacts with the capture antibody 473, the antigen-antibody reaction product remains as a confined signal element after washing. When the label-antigen complex does not react with the capture antibody 473, the capture antibody 473, which remains unreacted, serves as a released signal element. The capacitances and impedances of the cleaved signal elements are measured from their frequency response characteristics.

The left sectional view of FIG. 13 shows a state where the signal elements labeled with gold, latex, a fluorescent material, an enzyme, or a radioactive isotope, which are products of antigen-antibody reactions in the DBD 100, remain on the substrate 701 after washing. The right sectional view of FIG. 13 shows a state where no antigen-antibody reaction takes place and only the capture antibody remains unreacted after washing. A differential capacitance and impedance signal or a differential coloring information between the two states is detected by the interdigitated array electrodes 702, 703 or the image sensor 144.

FIG. 14 illustrates an image sensor for detecting analyte-specific signals from the assay site 132 of the DBD 100. The label-antigen complex is applied to an assay site 312 in which capture antibodies 473 are immobilized on the substrate 701. The image sensor obtains coloring information based on antigen-antibody reaction between the label-antigen complex and the capture antibody 473. The labeled antibody 471 is labeled with coloring moiety 474 made of, preferably, gold, latex, a fluorescent material, an enzyme, or a radioactive isotope. The substrate 701 may be preferably a porous membrane which may be one selected from NC (nitrocellulose) membrane, a nylon membrane, and aligned nanotubes.

When the label-antigen complex reacts with the capture antibody 473, the antigen-antibody reaction product remains as a confined signal element after washing. When the label-antigen complex does not react with the capture antibody 473, the capture antibody 473, which remains unreacted, serves as a released signal element. The left sectional view of FIG. 14 shows a state where the signal elements labeled with gold, latex, a fluorescent material, an enzyme, or a radioactive isotope, which are products of antigen-antibody reactions in the DBD 100, remain on the substrate 701 after washing. The right sectional view of FIG. 14 shows a state where no antigen-antibody reaction takes place and only the capture antibody remains unreacted after washing. A differential coloring information between the two states is detected by the image sensor. In a case where the confined signal element of the assay site is labeled with a fluorescent marker or a radioactive isotope, the confined signal element is excited by the laser generation device and the detection of the excited signal element is performed by the image sensor 144.

FIG. 15 illustrates an embodiment of a lab-on-a-chip designed for antigen-antibody reaction, which can be integrated into the DBD 100. FIG. 16 illustrates an embodiment of an array in the assay site 132 of FIG. 15. In FIG. 15, reference numeral 130 denotes a preparation chamber for preparing a serum sample from blood injected via a sample inlet 121; reference numeral 132 denotes a chamber for antigen-antibody reaction, which is an assay site with immuno arrays immobilized thereon so as to analyze and diagnose an antigen, i.e., sample or analyte; and reference numeral 133 denotes a trash chamber for collecting wastes generated during washing. The assay site 132 may be constructed by fixing the capture antibodies between the interdigitated array electrodes coated on a porous membrane or on the porous membrane without the interdigitated array electrodes. The porous membrane may be one selected from NC (nitrocellulose) membrane, a nylon membrane, and aligned nanotubes.

The chambers for the main processes, such as sample preparation, antigen-antibody reaction, and washing, are arranged in a spiral formation from the center to the outer perimeter of the disc and are interconnected with each other, so as to induce natural fluid flow by centrifugal force to allow for sequential processes. In addition, reagent reservoir chambers are arranged in a spiral formation near the corresponding reaction chambers.

Reference numeral 129 denotes a washing or elution buffer reservoir, and reference numeral 142a denotes a labeled antibody reservoir. Labeled antibodies in reservoir 142a are labeled with coloring moiety made of, for example, gold, latex, a fluorescent material, an enzyme, or a radioactive isotope. Reference numerals 150, 152, 153, and 156 denote valves. Fluid flow in the DBD 100 is controlled by the centrifugal force generated as the DBD is rotated and by opening and closing the valves.

Preferably, the serum sample may be prepared by using a centrifugal force generated by rotation of the disc. In this case, the preparation chamber may have a shape of a conical beaker or a flask in order to facilitate separating serum in centrifugal separation and a channel at a neck portion in order to be connected to a next chamber. Therefore, when a centrifugal force is applied, a blood clot is collected in a circumferential outer space of the chamber and a serum is collected in a circumferential inner space of the chamber, so that the serum can be easily separated because the serum layer is relatively high compared to the blood clot layer. Next, the serum can be moved to the next chamber by slowly rotating the bio disc while opening the valve 152.

Reference numeral 173 denotes a balancing chamber or a balancing weight which makes a center of the disc weight-centered. If the DBD 100 that rotates in a high speed is in a misalign center of mass, the DBD 100 may be greatly shaken during high speed rotation. The balancing chamber or the balancing weight 173 is needed to prevent the shaking of the DBD 100 during high speed rotation.

The assay site 132 may be constructed by fixing the capture antibodies between the interdigitated array electrodes coated on a porous membrane or on the porous membrane without the interdigitated array electrodes. The porous membrane may be one selected from NC (nitrocellulose) membrane, a nylon membrane, and aligned nanotubes.

In the DBD of FIG. 15, the immuno probe array may be constructed by arraying tumor markers as a capture antibody on a substrate. More preferably, the immuno probe array may be constructed by arraying at least one tumor marker selected from AFP, PSA, CEA, CA19-9, CA125, and CA15-3 on the substrate. Further, the immuno probe array may be constructed by arraying at least one selected from myoglobin, CK-MB, and Troponin I (TnI) as a cardiac infraction marker and GS (Glutamine Synthetase) as an Alzheimer's disease marker.

Generally, in the initial state of cancer, the blood concentration of the tumor marker is not high and in a normal range. As the cancer being developed, the blood concentration of the tumor marker is increased and positively detected. In this concern, The DBD driver according to an aspect of embodiment may further include statistic software and storage means for managing a history of the detection results of the assay site and provides periodical diagnosis information to a user. In addition, the DBD driver according to an aspect of embodiment may further include a software for determining a negative, positive, or dangerous state and calculating an associated value by detecting signal intensity by using the detection device. For example, the image sensor may measure an intensity of coloring by analyzing image information on a coloring particle.

In the DBD 100, the fluid movement may be controlled by a centrifugal force due to rotation of the DBD and opening and closing of the valve; a centrifugal force due to rotation of the DBD and hydrophilic affinity of the hydrophilic channel and opening and closing of the valve; or a centrifugal force due to rotation of the DBD and hydrophilic affinity of the hydrophilic channel with rapid and repetitive opening and closing of the valve. For the fluid movement to the hydrophilic channel, an initial resistance which is generated at the interface between hydrophobic coating and hydrophilic coating should be overcome. The rapid and repetitive opening and closing of the valve induce a shaking in the fluid and help the fluid movement to overcome the initial resistance. After the resistance is overcome, the fluid can be moved into the hydrophilic channel by hydrophilic affinity.

In the DBD 100, the fluid movement may be performed by a centrifugal force generated from rotation of the DBD and a "pulse value operation" where the valves are repeatedly opened at the time that the holes of the valves are aligned with the permanent magnet 5$a$ disposed on the slider 211 during rotation of the DBD. The valve operation is called a "pulse valve operation".

In FIG. 15, radial distances from the center of the DBD to the valves 151, 152, 153 and the outer dead zone of the DBD are referred to as R1, R2, R3 and R4 respectively. The radial distances have a relationship of R1<R2<R3<R4.

In order to open the valve 151 according to the "pulse valve operation", the permanent magnet 5$a$ on the slider 211 is moved to a radial distance of R1 and the DBD is rotated. The valve 151 is repeatedly opened by an attractive force at the time that the holes of the valves are aligned with the permanent magnet 5$a$ disposed on the slider during rotation of the disc. Further, the fluid movement may be performed by a centrifugal force generated from rotation of the DBD with the valve 151 repeatedly opened.

In order to close the valves according to the "pulse valve operation", the permanent magnet 5$a$ on the slider 211 is moved to a radial distance of R4. The valves 151, 152, 152 cannot be influenced by the permanent magnet 5$a$ at a radial distance of R4. However, the valves are closed by attractive forces between the film-like cylindrical magnets 7$a$, 7$b$, 7$c$ and permanent magnets 4$a$, 4$b$, 4$c$ disposed above the valves.

In the DBD 100, the fluid movement can be performed by a "pumping fluid movement" wherein repetition of the rapid approaching and separating movements of the permanent magnet 5$a$ on the slider 211 with respect to the center of the hole causes up and down movements of the film-like cylindrical magnet. Due to the up and down movements of the film-like cylindrical magnet, a pumping force is generated and exerted on the fluid, so that the fluid can flow. The fluid movement by the pumping force is called a "pumping fluid movement". The pumping fluid movement can be useful in a case where a centrifugal force cannot be used for the just-before valve of the assay site.

The pumping fluid movement may be performed after a "radial valve searching process" or an "azimuthal valve searching process" so as for the permanent magnet on the slider to precisely address the hole.

(1) The radial valve searching process is performed by movement of the slider. For example, the permanent magnet 5$a$ on the slider 211 is moved to a radial distance R1, R2, R3 or R4 from the center of the DBD. (2) Then, the azimuthal valve searching process is performed by rotation of the disc. For example, the azimuthal valve searching process is performed by slow rotation of the spindle motor 102 or repetition of short rotations of the spindle motor 102 due to a small torque with the slider 211 stopped. During the slow rotation or several times of the short rotations, when the film-like cylindrical magnet located at the center of the hole is aligned with the movable permanent magnet 5$a$ disposed on the slider 211, the slow or short rotation of the disc is stopped by a strong attraction therebetween, so that the disc is stopped at the associated position.

After the movable permanent magnet 5$a$ disposed on the slider 211 is aligned with the center of the hole by the "radial valve searching process" or "azimuthal valve searching process", the film-like cylindrical magnet is moved up and down and generate a pumping force by the "pumping fluid movement", so that the fluid can flow.

FIG. 15 may be modified into a DBD for diagnosing diabetes.

To detect a recent 2-3 months blood sugar level, anti-HbA1c antibody or glucose antibody is arrayed on the assay site 132 in the DBD 100. The amount of HbA1c or glucose is measured by an image sensor which can detect coloring information. Total amount of hemoglobin may be measured by detecting a coloring intensity of the hemoglobin. The blood sugar level may be calculated in % HBA1c (HbA1c/total Hemoglobin×100).

In FIG. 15, reference numeral 130 denotes a preparation chamber for preparing a serum or hemoglobin sample from blood injected via a sample inlet 121; reference numeral 132 denotes a chamber for antigen-antibody reaction chamber where anti-HbA1c antibody or glucose antibody is arrayed on the assay site to react with an antigen, glucose, or HbA1c in the prepared sample; and reference numeral 133 denotes a trash chamber for collecting wastes generated during washing. The preparation chamber may further contain an RBC (Red blood Cell) lysis buffer solution used to destruct red blood cells and extract hemoglobin.

The assay site 132 may be constructed by fixing the capture antibodies between the interdigitated array electrodes coated on a porous membrane or on the porous membrane without the interdigitated array electrodes. The porous membrane may be one selected from NC (nitrocellulose) membrane, a nylon membrane, and aligned nanotubes.

Reference numeral 129 denotes a washing or elution buffer reservoir, and reference numeral 142$a$ denotes a labeled antibody reservoir. Labeled antibodies in reservoir 142$a$ are labeled with coloring moiety made of, for example, gold, latex, a fluorescent material, an enzyme, or a radioactive isotope. In a case where the label is enzyme, the DBD may further include a substrate chamber 134 for reserving a substrate which reacts with the enzyme.

In FIG. 15, the DBD 100 may further include a vinyl cover or a protective vinyl which closes at least one of the sample inlet 121, the venting holes 12a, 12b, 12c, and the reagent inlet 13a, 13b. Since the vinyl cover has a tendency to adhere to the DBD, the vinyl cover can protect a surface of the DBD and close all the holes (the venting hole and the reagent inlet or optionally the sample inlet). Just before use of the DBD, the vinyl cover is uncovered from the DBD, so that the venting hole or the sample inlet can be opened and exposed. At this time, the reagent inlet is not opened. In addition, after a reagent is injected into the chamber, the reagent inlet can be sealed with a UV adhesive or a vinyl cover (protective cover) separate from the uncovered vinyl cover.

FIG. 16 illustrates an embodiment of the assay site in which the tumor markers are arrayed in spots on the substrate such as the porous membrane 999 or polycarbonate. In this example, 6 tumor markers, AFP (999a), PSA (999b), CEA (999c), CA19-9 (999d), CA125 (999e), and CA15-3 (999f) are arrayed on the porous membrane 999. For the detailed descriptions on the method for fixing the antibody on the polycarbonate, International Patent Application No. PCT/KR02/00126 filed 27 Jan. 2002 and its priority Korean Patent Application No. 10-2001-0003956 filed 27 Jan. 2001, which are entitled "Nucleic acid hybridization assay method and device using cleavage technique responsive to complementary double strand or single strand of nucleic acids or oligonucleotides" can be referred to.

FIG. 17 illustrates an embodiment of a assay site which is connected with a hydrophilic channel and a just-before valve according to an aspect of embodiment. In FIG. 17, reference numeral 901a denotes a hydrophobic channel, reference numeral 901b denotes a hydrophilic channel and reference numeral 153 denotes a just-before valve of the assay site. Reference numeral 999 denotes a porous membrane fixed with capture antibodies in the assay site. In this embodiment, the hydrophilic channel 901b is divided into 3 branch channels, and the hydrophilic channel 901b is connected to the porous membrane 999 through holes 610a, 610b, 610c provided to a distal end of each branch channel. The assay site has air holes 915a and 915b disposed at the both sides of the assay site to dry the porous membrane 999 when the disc is rotated.

After antigens in the serum are bound with the labeled antibody in the label chamber 142a, label-antigen complexes are formed and flow into the hydrophobic channel 901b and fill the branched channels when the valve 153 is opened. Next, the valve 153 is closed and the bio disc is slowly rotated to move the label-antigen complex into the porous membrane 999 through holes 610a, 610b, 610c provided to a distal end of each branch channel. And then, an antigen-antibody reaction between the label-antigen complex and the capture antibodies fixed in the porous membrane 999 is performed.

An embodiment of how to conduct main assay processes in the labs-on-a-chip of FIG. 15 will be described.

<Sample Preparation Process>

Serum is extracted from blood in the preparation chamber 130 in the following way.

1) 10 µL (EDTA, ACD Tube) of blood is injected via the sample inlet 121 into the preparation chamber 130. The bio disc is slowly rotated to separate a serum from a blood clot.

2) The valve 151 is opened, and the DBD is slowly rotated to allow the serum in the upper layer of the preparation chamber 130 to flow into the labeled antibody reservoir 142a. The opening of the valve 151 is performed by moving the permanent magnet 5a to a radial distance R1 from a center of the DBD and based on the "pulse valve operation".

3) Rotation of the DBD is stopped, and the valve 151 is closed. The closing of the valve 151 is performed by moving the permanent magnet 5a to a radial distance R4 from a center of the DBD.

<Antigen-Antibody Reaction>

The labeled antibody reservoir 142a of FIG. 15 reserves labeled antibodies labeled with coloring moiety, such as gold, latex, a fluorescent material, an enzyme, and a radioactive isotope and the assay site 132 contains capture antibodies immobilized on a substrate such as porous membrane.

Antigen-antibody reactions in a DBD according to an aspect of embodiment involve binding an antigen in the serum extracted via the sample preparation to the labeled antibodies in the labeled antibody reservoir 142a to form a label-antigen complex and binding the label-antigen complex to the capture antibodies in the assay site 132. These antigen-antibody reactions are induced in the following way.

1) After the serum enters the labeled antibody reservoir chamber 142, the labeled antibody reservoir chamber 142 is incubated for 1-2 minutes to induce a reaction between an antigen and labeled antibodies to form a label-antigen complex.

2) The valve 152 is opened, the DBD is slowly rotated to allow the label-antigen complex in the labeled antibody reservoir 142a to flow into the assay site 132.

3) Rotation of the DBD is stopped, and the valve 152 is closed.

4) The DBD is incubated in a stationary state at room temperature for 3-5 minutes and left for a reaction between the label-antigen antibody and the capture antibodies in the assay site 132.

5) The DBD is rotated, and the valve 153 is opened to allow the washing buffer or elution buffer in the washing buffer reservoir 129 to enter and wash the assay site 132.

The incubation in the step 1) may further include a warbling mixing process induced by short forward and backward movements of the slider 211 after "azimuthal valve searching process" or short rotations of the DBD with a small torque The movement of label-antigen complex in the step 2) may performed by the "pumping fluid movement" after a "radial valve searching process" or an "azimuthal valve searching process".

The movement of washing or elution buffer in the step 5) may be performed by the "pumping fluid movement" after a "radial valve searching process" or an "azimuthal valve searching process".

The antigen-antibody reaction may further include, before the detecting of the assay site, cleaning and drying the assay site by a high speed rotation of the DBD.

<Detection Process and Remote Diagnosis>

Uncleaved signal elements remaining in the assay site 132 are detected using a detector including an optical device, an electrochemical device, a capacitance and impedance measurement device, an image sensor, or a bio-pit detection device, which have the above-described structure, the detector being programmed to be able to selectively detect assay sites with cleavable signal elements.

The diagnostic data and a questionnaire sheet based on the result of the detection are displayed on a computer monitor, and optionally automatically or manually transmitted through the Internet to a specialist at a remote location. The patient waits for a prescription from the specialist.

An assay automatically starts as soon as a DBD 100 is loaded into a bio-driver apparatus. When a DBD into which a sample has not been injected yet via the sample inlet 121 is loaded, the bio-driver apparatus sends an "eject" message or a warning message to a user.

To determine whether a sample has been injected or not, an additional impedance measurement device may be installed in the preparation chamber 130. Whether a sample has been injected or not can be determined from different impedance characteristics between two states, one containing a sample and one without a sample.

Such an impedance measurement device for detecting the presence of a sample may be implemented with interdigitated array electrodes, like the capacitance and impedance measurement device installed in the assay site 132.

When an unloading or a stop command is input to the bio-driver apparatus during assay or diagnosis, the bio-driver apparatus sends a warning message or requests a user's password while continuing assay and diagnosis. If the user enters the correct password, the bio-driver apparatus stops the assay or diagnosis and ejects the DBD.

Once the assay or diagnosis is completed, the bio-driver apparatus ejects the DBD at the request of the user.

The DBD stores in its RFIC card 188 information on how many times it has been used, its validation period, and kinds of diseases which it can diagnose. For example, when an eject command is input to a disposable DBD during an assay or after the completion of an assay, the history of its use is written to its RFIC card 188 to later inform a user who loads the disposable DBD that it cannot be reused. When a DBD which has an expired validation term is loaded, the bio-driver apparatus informs the user that the DBD is no longer valid. For example, a computer may calculate the time interval between the production date and the present date and determine the expiration of validation term.

FIGS. 18 and 19 illustrate exemplary appearances of front loading-type bio-driver apparatuses according to an aspect of embodiment. Reference numeral 751 denotes a case, reference numeral 750 denotes a DBD loading tray, and reference numerals 745 and 746 denote a button and a stop button, respectively, for general optical discs.

In particular, the DBD driver apparatus of FIG. 18 is an embodiment of indicating the status of proceeding with an assay using light emitting diodes (LEDs). A LED 741 indicates that a currently loaded disc is a DBD, a LED 742 indicates the current status of proceeding with an assay, and a LED 743 indicates that a general optical disc has been loaded. Alternative indicative means instead of LEDs can be used for the same purpose.

The DBD driver apparatus of FIG. 19 is an embodiment of indicating the status of proceeding with an assay through a liquid crystal display (LCD) 760. In this embodiment, the status of progress in each main process, such as sample preparation, PCR, hybridization, and antigen-antibody reaction, can be expressed in percentages or as a bar graph.

The status of proceeding with an assay in the bio drive apparatus according to an aspect of embodiment can be displayed through a computer monitor or a graphic user interface. The status of progress in each main process, such as sample preparation, PCR, hybridization, and antigen-antibody reaction, can be expressed in percentages or as a bar or pie graph.

FIG. 20 illustrates an exemplary appearance of top loading-type DBD driver apparatuses according to an aspect of embodiment. Reference numeral 751 denotes a case, reference numeral 750a denotes a DBD loading cover, reference numeral 760 denote a liquid crystal display, and reference numeral 741, 742, 743 are light emitting diodes (LEDs) indicating the status of proceeding with an assay.

FIG. 21 illustrates an exemplary appearance of DBD driver apparatuses having a plurality of turn tables (777a, 777b, 777c, 777d) so as to load a plurality of the DBDs in one time. In this case, 4 bio discs can be assayed in order or in one time.

FIG. 22 illustrates and exemplary appearance of DBD driver apparatuses having double deck drivers which can load the DBD for diagnosis and a DVD disc for movies.

Alternatively, the DBD driver apparatus may be a combo driver having a DBD driver at one side and a VCR (Video Cassette Recorder) at the other side. Accordingly, a movie can be seen during the diagnosis.

Reference numerals 750a and 750b denote a DBD or DVD loading tray. Reference numerals 745a and 745b denote a play and search button and reference numerals 746a and 746b denote a stop button for general optical discs. References 760a and 760b denote light emitting diodes (LEDs) indicating the status of proceeding with an assay.

While an aspect of embodiment has been particularly shown and described with reference to exemplary embodiments thereof, it will be understood by those of ordinary skill in the art that various changes in form and details may be made therein without departing from the spirit and scope of an aspect of embodiment as defined by the following claims.

INDUSTRIAL APPLICABILITY

As described above, a DBD device including a new valve control means and fluid movement system, a DBD driver apparatus, and an assay method using the same according to an aspect of embodiment are suitable for labs-on-a-chip for various diagnostic assay devices, nucleic acid hybridization assay devices, and immunoassays. A particularly important feature of an aspect of embodiment is that the bio-driver apparatus is compatible with general optical discs, including audio CDs, game CDs, including CD-ROMs, DVD players, etc. Thus, an aspect of embodiment offers an economical and convenient alternative to conventional products. In addition, the bio-driver apparatus can be readily and easily applied in connection with a computer for remote diagnosis via the Internet.

Although a few embodiments have been shown and described, it would be appreciated by those skilled in the art that changes may be made in these embodiments without departing from the principles and spirit of the invention, the scope of which is defined in the claims and their equivalents.

The invention claimed is:

1. A digital bio-disc (DBD) comprising: a rotatable disk having a rotation axis, where the rotatable disk comprises:
   a sample inlet; chambers which reserve a buffer solution or a reaction solution, a nitrocellulose membrane where bio materials are arrayed, air holes disposed at both sides of the nitrocellulose membrane to dry the nitrocellulose membrane, hydrophobic channels through which fluid can flow between the sample inlet, and the chambers by centrifugal force, a hydrophilic channel formed between the chamber connected to the nitrocellulose membrane, and valve holes formed in a direction parallel to the rotation axis;
   a cylindrical permanent magnet placed on the valve holes, wherein the cylindrical permanent magnet is capable of opening and closing the valve hole by moving upward or downward in a direction parallel to the rotation axis;
   a plurality of non-movable permanent magnets closing the valve holes, wherein the non-movable permanent magnets are fixed above each of the valve holes; and a single movable permanent magnet capable of selective opening one of the valve holes, wherein the valve hole is opened only when the single movable permanent magnet is vertically aligned to the non-movable magnet, wherein the single movable permanent magnet is mounted on a radially movable slider disposed under the DBD.

2. The DBD according to claim 1, wherein the chamber further comprise a venting hole and/or a reagent inlet.

3. The DBD according to claim 2, wherein the DBD further comprise a vinyl cover or a protective vinyl which closes at least one of the sample inlet, the venting hole, and the reagent inlet.

4. The DBD according to claim 1, wherein the DBD further comprise a balancing chamber or a balancing weight which makes a center of the disc weight-centered.

5. The DBD according to claim 1, wherein the cylindrical permanent magnet is coated with a cushion material or a film-like cushion material is inserted between the cylindrical permanent magnet and the valve hole.

6. The DBD according to claim 1, wherein the fluid movement is performed by a "pumping fluid movement" that the single permanent magnet on the slider repeatedly performs rapid approaching and separating movements with respect to the center of the valve hole.

7. The DBD according to claim 6, wherein the pumping fluid movement is performed after a "radial valve searching process" or an "azimuthal valve searching process".

8. The DBD according to claim 1, the fluid movement is performed by a centrifugal force generated from rotation of the disc and a "pulse valve operation" where the valve holes are repeatedly opened whenever the cylindrical permanent magnet is aligned with the single permanent magnet disposed on the slider during rotation of the disc.

9. The DBD according to claim 1, wherein the substrate in the assay site is a porous membrane, a before channel of a just-before valve of the assay site is a hydrophobic channel, and an after channel of the just-before valve is a hydrophilic channel.

10. The DBD according to claim 9, wherein the porous membrane is one selected from a group consisting a NC (nitrocellulose) membrane, a nylon membrane, and an aligned nanotubes.

11. The DBD according to claim 9, wherein the hydrophilic channel is constructed by coating a surface of a hydrophobic channel with a hydrophilic acrylate, an ultra-hydrophilic poly (N-isopropylacrylamide) (PIPAAm) or an optical catalyst selected from a group consisting $ZrO_2$, $ZnO$, $Fe_2O_3$, and $TiO_2$ or by performing a surface modification on the hydrophobic channel with plasma.

12. The DBD according to claim 9, wherein the hydrophilic channel is divided into at least one branch channel, and the hydrophilic channel is connected to the porous membrane through a hole provided to a distal end of the branch channel.

13. The DBD according to claim 9, wherein the assay site may have air holes disposed at the both sides of the assay site to dry the porous membrane.

14. The DBD according to claim 9, wherein the fluid movement into the assay site is performed by the opening of the just before valve and hydrophilic affinity of the hydrophilic channel and the reaction solution without using a centrifugal force.

15. The DBD according to claim 1, wherein the body of the DBD is constructed with an upper substrate, an intermediate substrate, and a lower substrate, and these substrates are adhered and assembled by using ultrasonic fusing, UV adhesive, or double-sided tape to form a single body.

16. The DBD according to claim 1, wherein the bio material is at least one selected from DNA, oligo-nucleotide, RNA, PNA, ligand, receptor, antigen, antibody, and protein.

17. The DBD according to claim 1, wherein the chamber comprises at least one selected from the group consisting of: a preparation chamber for preparing a DNA sample from blood, cells, or RNA; a PCR chamber for amplifying the DNA sample through a polymerase chain reaction (PCR); a hybridization chamber in which assay and diagnostic probes are arrayed on the substrate for hybridization with the amplified DNA from the PCR; and a trash chamber for collecting wastes generated from washing.

18. The DBD according to claim 17, wherein the preparation chamber reserves a lysis buffer solution used to destruct a cell and extract a DNA through lysis and particles or ferromagnetic beads having affinity to the extracted DNA.

19. The DBD according to claim 17, wherein the DBD comprises a plurality of the PCR chambers and each PCR chamber reserves one type or several types of primer, or all the PCR chambers reserves the same type of primer.

20. The DBD according to claim 17, wherein the preparation chamber reserves only a lysis buffer solution used to destruct the cell and extract the DNA without using the particles or ferromagnetic beads so as to prepare the DNA sample by using a centrifugal force generated from rotation of the bio-disc.

21. The DBD according to claim 1, wherein the chamber comprises at least one chamber selected from the group consisting of: a preparation chamber for preparing a serum sample, an antigen, or an antibody from blood or cells; an antigen-antibody reaction chamber in which immuno probes are arrayed on the substrate for an antigen-antibody reaction with the prepared antigen or antibody; and a trash chamber for collecting waste generated from washing.

22. The DBD according to claim 21, wherein the immuno probe array is constructed by arraying at least one tumor marker selected from AFP, PSA, CEA, CA19-9, CA125, and CA15-3 on the substrate.

23. The DBD according to claim 21, wherein the immuno probe is at lease one selected from myoglobin, CK-MB, and Troponin I (Tn 1) as a cardiac infraction marker and GS (Glutamine Synthetase) as an Alzheimer's diseases marker.

24. The DBD according to claim 1, wherein the chamber comprises at least one chamber selected from the group consisting of: a preparation chamber for preparing a serum or hemoglobin sample from blood; an antigen-antibody reaction chamber where anti-HbA1c antibody or glucose antibody is arrayed on the assay site to react with an antigen, glucose, or HbA1c in the prepared sample; and a trash chamber for collecting wastes generated from washing.

25. The DBD according to claim 24, wherein the preparation chamber further contains an RBC (Red blood Cell) lysis buffer solution used to destruct red blood cells and extract hemoglobin.

26. The DBD according to claim 21, wherein, in the preparation chamber, the serum sample is be prepared by using a centrifugal force generated by rotation of the DBD.

27. The DBD according to claim 26, wherein the preparation chamber has a shape of a conical beaker, a flask, or a test tube in order to facilitate separating serum in centrifugal separation.

28. The DBD according to claim 21, wherein the DBD may further comprise a label chamber for reserving a labeled antibody.

29. The DBD according to claim 28, wherein the label is one selected a group consisting gold, latex, a fluorescent marker, an enzyme, and a radioactive isotope.

30. The DBD according to any one of claim 17, wherein the preparation chamber further comprise an impedance measuring device therein for checking whether or not a sample is injected into the preparation chamber.

31. The DBD according to claim 30, wherein the impedance measuring device is an interdigitated array.

32. The DBD according to claim 1, wherein the assay site comprises an immuno assay sector and a nucleic acid probe assay sector arranged in an angular or radial direction to enable an immuno assay and a nucleic acid probe assay to be performed concurrently.

33. The DBD according to claim 1, wherein the assay site is detected by a detection device coupled with a transforming device selected from a light transmission type measuring device, an electro-chemical detection device, a capacitance and impedance measuring device, an image sensor, or a bio-pit detection device.

34. The DBD according to claim 33, wherein the light transmission type detection device comprises: a laser device (light transmitting unit) which emits a laser beam onto a confined signal element and a released signal element; and an optical detector (light receiving unit) which detects a differential light transmission signal between the signal elements.

35. The DBD according to claim 34, wherein at least one optical detector (light receiving unit) is arrayed and integrated along a circumference of the DBD to correspond to each assay site.

36. The DBD according to claim 34, wherein at least one laser device (light transmitting unit) and at least one optical detector (light receiving unit) is arrayed and integrated along a circumference of the DBD to correspond to each assay site.

37. The DBD according to claim 33, wherein the electro-chemical detection device or the capacitance and impedance measuring device comprises: interdigitated array electrodes disposed on the substrate of the assay site; and a HRP (Horse Radish Peroxidase) and/or enzyme and/or a metal microsphere attached to the end of confined signal elements.

38. The DBD according to claim 37, wherein the interdigitated array electrodes is constructed by coating a surface of a porous membrane with a conductive material.

39. The DBD according to claim 33, wherein the image sensor picks up an image of a label (coloring particle) linked with the probe and obtains image information.

40. The DBD according to claim 39, wherein the coloring particle is excited by a laser generating device, and the excited image information on the assay site is obtained by the image sensor.

41. The DBD according to claim 33, wherein the bio-pit detection device is any one of an STM (Scanning Tunneling Microscope), an AFM (Atomic Force Microscope), a cantilever AFM, an MFM (Magnetic Force Microscope), and an SNOM (Scanning Near-field Optical Microscope).

42. The DBD according to claim 1, wherein the DBD further comprises a memory or other storage or RF IC for storing a protocol of the DBD, assay interpretive algorithms, standard control values for analysis, positional information on analysis sites, bioinformatics information, self-diagnostics, DBD driver software, educational information for patients on clinical assays, a variety of web sites and links enabling a patient to communicate with a doctor or hospital at a remote location based on his/her diagnosis result, or encrypted personal information.

43. The DBD according to claim 1, wherein the DBD further comprises an RF IC which transmits a detection result of the assay site obtained by the detection device to an external central controller, a storage device, or an input output device through an RF interface.

44. The DBD according to claim 43, wherein the RF IC includes a condenser for storing a sufficient amount of electricity generated from an induction coil embedded in the DBD through an external RF wave.

45. A DBD driver apparatus comprising: a turntable on which the DBD according to claim 1 is mounted; a spindle motor which rotates the DBD; a slider which includes a detector device for detecting the assay site in the DBD and a permanent magnet for controlling opening and closing of the valves in the DBD; a slide motor which controls moving of the slider; a central controller which controls whole components of the DBD driver; and a body which supports the DBD driver.

46. The DBD driver apparatus according to claim 45, wherein the detector device is one selected from a light transmittance measuring device, an electro-chemical detection device, a capacitance and impedance measuring device, an image sensor, and a bio-pit detection device.

47. The DBD driver apparatus according to claim 46, wherein the image sensor is a line image sensor for sensing a light intensity in units of a pixel.

48. The DBD driver apparatus according to claim 47, wherein the line image sensor is a linear sensor array or a CIS (Contact Image Sensor).

49. The DBD driver apparatus according to claim 47, wherein the line image sensor further includes a light emitting diode (LED) for illumination with a wavelength of from 500 nm to 800 nm and an optical lens which are disposed in the vicinity of the line image sensor.

50. The DBD driver apparatus according to claim 47, wherein the line image sensor is moved on the slider to obtain two-dimensional image information of the assay site.

51. The DBD driver apparatus according to claim 45, wherein the slider is provided with a bio optical pickup module (BOPM) device including the detection device for detecting the assay site and a general optical device (a CD reader or a DVD reader) in a module.

52. The DBD driver apparatus according to claim 45, wherein the slider is connected to the slide motor through a worm gear so that the moving thereof is controlled.

53. The DBD driver apparatus according to claim 51, wherein the bio optical pickup module (BOPM) device further comprises contact interface for supplying a control signal to the assay site in the DBD and reading a detection signal from the assay site in the DBD.

54. The DBD driver apparatus according to claim 45, wherein the fluid movement in the DBD is performed by a "pumping movement" that a permanent magnet on the slider repeatedly performs rapid approaching and separating movements with respect to the center of the hole, with the rotation of the disc stopped.

55. The DBD driver apparatus according to claim 54, wherein the pumping fluid movement is performed after a "radial valve searching process" or an "azimuthal valve searching process".

56. The DBD driver apparatus according to claim 45, wherein the fluid movement in the DBD is performed by a centrifugal force generated from rotation of the disc and a "pulse value operation" where the valves are repeatedly opened at the time that the holes of the valves are aligned with the permanent magnet disposed on the slider during rotation of the disc.

57. The DBD driver apparatus according to claim 45, wherein a circuit board on which a central controller and a storage device or an input output device are disposed is engaged with the DBD driver body, and the central controller rotates and stops the spindle motor at the time of rotating and stopping the DBD and rotates and stops the slide motor for controlling moving of a detector device for detection of the assay site in the DBD and a permanent magnet for control of opening and closing of the valves in the DBD.

58. The DBD driver apparatus according to claim 57, wherein the input output device is a USB (Universal Serial Bus) device or a device according to IEEE-1394, ATAPI or Internet communication standard.

59. The DBD driver apparatus according to claim 45, wherein the DBD driver apparatus further comprises an RF wave generation unit for supplying power to the RF IC on the DBD.

60. The DBD driver apparatus according to claim 51, wherein the DBD driver apparatus further comprises a bio-disc detection unit for determining whether a currently loaded disc is a DBD or a general optical disc selected from among an audio CD, a CD-R, a game CD, and a DVD.

61. The DBD driver apparatus according to claim 51, wherein an optical pickup device reads a groove pattern or a data pattern at a particular area on a surface of the DBD to allow the central controller to recognize that a disc currently loaded on the DBD driver is a DBD.

62. The DBD driver apparatus according to claim 51, wherein the central controller may determine whether a currently loaded disc is a DBD or a general optical disc selected from among an audio CD, a CD-R, a game CD, and a DVD; transmit information read from the general optical disc using the optical pickup to a storage or output unit, transmit information to be written to the optical pickup device, or output various control signals required for read/write if the currently loaded disc is determined to be a general optical disc; and transmit various control signals for control of the DBD to the bio optical pickup (BOPM) device or the RF IC if the currently loaded disc is determined to be a DBD.

63. The DBD driver apparatus according to claim 51, wherein, at the time of loading the DBD, a new loading of the DBD is transmitted to the central controller in a wireless manner through a non-contact interface or an RF IC on the DBD, so that the central controller recognizes that the disc loaded on the DBD driver is the DBD.

64. The DBD driver apparatus according to claim 45, wherein the DBD driver apparatus sends an eject message or a warning message to a user if a DBD into which a sample has not be injected is loaded.

65. The DBD driver apparatus according to claim 45, wherein, when an eject (unloading) or a stop command is input to the DBD driver apparatus during assay or diagnosis, the DBD driver apparatus sends a warning message or requests a user's password while continuing assay and diagnosis.

66. The DBD driver apparatus according to claim 45, wherein the DBD driver apparatus further comprises a memory storing information on how many times a DBD has been used, its validation period, and kinds of diseases which it can diagnose, so as to provide a user with the stored information on the DBD or the availability of the DBD whenever the DBD is loaded.

67. The DBD driver apparatus according to claim 45, wherein the DBD driver apparatus further comprises statistic software and storage to manage a history of the detection results of the assay site and provides periodical diagnosis information to a user.

68. The DBD driver apparatus according to claim 45, wherein the DBD driver apparatus further comprises software for determining a negative, positive, or dangerous state and calculating an associated value by detecting signal intensity by using the detection device.

69. The DBD driver apparatus according to claim 51, wherein the DBD driver apparatus further comprises: a play and search button and a stop button for general optical discs; and a light emitting diode (LED) indicating that a DBD has been loaded.

70. The DBD driver apparatus according to claim 45, wherein the DBD driver apparatus further comprises a liquid crystal display or a monitor to display the status of progress in main processes performed in the DBD in percentages or as a bar graph or a pie graph.

71. The DBD driver apparatus according to claim 45, wherein the body which supports the DBD driver allows DBD top loading or DBD front loading.

72. The DBD driver apparatus according to claim 45, wherein the DBD driver apparatus has a plurality of turn tables so as to load a plurality of the DBDs in one time.

73. The DBD driver apparatus according to claim 45, wherein the DBD driver apparatus is a double deck driver so as to load the DBD for diagnosis and a DVD disc for movies.

74. The DBD driver apparatus according to claim 45, wherein the DBD driver apparatus is a combo driver having a DBD driver at one side and a VCR (Video Cassette Recorder) at the other side.

75. A nucleic acid assay method using a DBD according to claim 17, the method comprising: preparing a DNA sample from blood, cells, or RNA; amplifying the prepared DNA through polymerase chain reaction (PCR); hybridizing amplified DNA products from the PCR with the assay and diagnostic probe arrayed on the assay site; and detecting a result of hybridization reaction in the assay site by using a detection device coupled with a transforming device, wherein the detection device includes a light transmission type measuring device, an electro-chemical detection device, a capacitance and impedance measuring device, an image sensor, or a bio-pit detection device.

76. The nucleic acid assay method according to claim 75, wherein the preparing of the DNA sample may comprises: injecting blood via a sample inlet into the preparation chamber; performing incubation in the preparation chamber to allow particles or ferromagnetic beads in the preparation chamber to attract DNA extracted through lysis; fixing the particles or ferromagnetic beads and slowly rotating the DBD to wash out and flow the cell debris into the trash chamber; and separating the DNA from the particles or ferromagnetic beads or resuspending the DNA in a resuspension buffer.

77. The nucleic acid assay method according to claim 75, wherein the amplifying of the prepared DNA sample through PCR may comprises: rotating the DBD to allow the prepared DNA sample to flow into the PCR chamber; and repeating a PCR cycle several times using a heater and a thermo-sensor installed in the PCR chamber to amplify the DNA sample.

78. The nucleic acid assay method according to claim 75, wherein the method further comprises, after the PRC process: rotating the DBD to allow a DNAse to flow into the PCR chamber; and heating the PCR chamber at a high temperature to deactivate the DNAse and form single-stranded DNA fragments (denaturing process).

79. The nucleic acid assay method according to claim 75, wherein each PCR chamber may comprise a heater which is controlled independently from the heaters of the other PCR chambers (in independent incubation time intervals) to form the DNA fragments having different lengths.

80. An immuno assay method using the DBD according to claim 21, the method comprising: rotating the DBD at high speed to extract serum or an antigen from blood; introducing the extracted antigen into a label chamber and performing incubation in the chamber for 1-2 minutes to bind the antigen to labeled antibodies and form a label-antigen complex; moving the label-antigen complex into the assay site; and performing cultivation in the DBD in a stationary state to induce an antigen-antibody reaction between the label-antigen complex and the capture antibodies; and adding a washing buffer and washing the assay site; and optionally detecting the assay site by using a detection device coupled with a transforming device, wherein the detection device includes a light transmission type measuring device, an electro-chemical detection device, a capacitance and impedance measuring device, an image sensor, or a bio-pit detection device.

81. An immuno assay method using the DBD according to claim 24 for diabetes diagnosis or blood sugar level analysis, the method comprising: preparing serum or hemoglobin from blood; introducing the prepared antigen into a label chamber and performing incubation in the chamber for 1-2 minutes to bind the antigen to labeled antibodies and form a label-antigen complex; moving the label-antigen complex into the assay site; and performing cultivation in the DBD in a stationary state to induce an antigen-antibody reaction between the label-antigen complex and the capture antibodies; and adding a washing buffer and washing the assay site; and optionally detecting the assay site by using a detection device coupled with a transforming device, wherein the detection device includes a light transmission type measuring device, an electro-chemical detection device, a capacitance and impedance measuring device, an image sensor, or a bio-pit detection device.

82. The assay method according to claim 75, wherein the method further comprises, before the detecting of the assay site, cleaning and drying the assay site.

83. The assay method according to claim 75, wherein the method further comprises a warbling mixing process in the performing of the incubation, the cultivation, the hybridizing, or the antigen-antibody reaction.

84. The assay method according to claim 75, wherein, in the moving of the label-antigen complex or the DNA into the assay site, the label-antigen complex or the DNA is allowed to flow into a porous membrane of the assay site by opening a just-before valve of the assay site and using a hydrophilic affinity of a hydrophilic channel without a centrifugal force.

85. The assay method according to claim 84, wherein the method further comprises, after the performing cultivation to induce an antigen-antibody reaction or hybridization reaction between the label-antigen complex or the DNA and the capture antibodies on the porous membrane, drying the porous membrane by a high speed rotation of the disc.

86. The assay method according to claim 85, wherein the method further comprises, after the drying, moving a washing buffer by opening a just-before valve of the assay site and using a hydrophilic affinity of a hydrophilic channel and cleaning the assay site by using the washing buffer.

87. The assay method according to claim 86, wherein the method further comprises, after the cleaning, drying the porous membrane by a high speed rotation of the disc.

88. The assay method according to claim 75, wherein, the method further comprises a remote diagnosis step where the diagnostic data based on the result of the detection are displayed on a computer monitor, the diagnostic result together with a questionnaire sheet is optionally automatically or manually transmitted through the Internet to a specialist at a remote location, and the patient waits for a prescription from the specialist.

* * * * *

UNITED STATES PATENT AND TRADEMARK OFFICE
CERTIFICATE OF CORRECTION

| | | |
|---|---|---|
| PATENT NO. | : 8,263,386 B2 | Page 1 of 1 |
| APPLICATION NO. | : 11/919931 | |
| DATED | : September 11, 2012 | |
| INVENTOR(S) | : Jae Chern Yoo | |

It is certified that error appears in the above-identified patent and that said Letters Patent is hereby corrected as shown below:

Column 34, Line 36, In Claim 23, delete "lease" and insert -- least --, therefor.
Column 34, Line 64, In Claim 30, after "to" delete "any one of".
Column 36, Line 55, In Claim 56, delete "value" and insert -- valve --, therefor.
Column 38, Line 13-14, In Claim 72, delete "turn tables" and insert -- turntables --, therefor.

Signed and Sealed this
Twentieth Day of November, 2012

David J. Kappos
*Director of the United States Patent and Trademark Office*